(12) United States Patent
Varghese et al.

(10) Patent No.: US 12,054,557 B2
(45) Date of Patent: Aug. 6, 2024

(54) COMBINATION OF ANTI-PD-1 ANTIBODIES AND BISPECIFIC ANTI-CD20/ANTI-CD3 ANTIBODIES TO TREAT CANCER

(71) Applicant: Regeneron Pharmaceuticals, Inc., Tarrytown, NY (US)

(72) Inventors: Bindu Varghese, Hopewell Junction, NY (US); Gavin Thurston, Briarcliff Manor, NY (US); Israel Lowy, Dobbs Ferry, NY (US); Carrie Brownstein, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 338 days.

(21) Appl. No.: 17/210,860

(22) Filed: Mar. 24, 2021

(65) Prior Publication Data

US 2021/0214457 A1    Jul. 15, 2021

Related U.S. Application Data

(63) Continuation of application No. 15/386,453, filed on Dec. 21, 2016, now abandoned.

(60) Provisional application No. 62/270,749, filed on Dec. 22, 2015.

(51) Int. Cl.
| C07K 16/28 | (2006.01) |
| A61K 39/395 | (2006.01) |
| A61K 45/06 | (2006.01) |
| C07K 16/30 | (2006.01) |
| A61K 39/00 | (2006.01) |

(52) U.S. Cl.
CPC ...... *C07K 16/2887* (2013.01); *A61K 39/3955* (2013.01); *A61K 45/06* (2013.01); *C07K 16/2809* (2013.01); *C07K 16/2818* (2013.01); *C07K 16/3061* (2013.01); *A61K 2039/505* (2013.01); *C07K 2317/31* (2013.01); *C07K 2317/565* (2013.01)

(58) Field of Classification Search
CPC ............ C07K 16/2887; C07K 16/2809; C07K 16/2818; C07K 16/3061; C07K 2317/31; C07K 2317/565; A61K 39/3955; A61K 45/06; A61K 2039/505; A61P 35/00; A61P 35/02; A61P 43/00
See application file for complete search history.

(56) References Cited

U.S. PATENT DOCUMENTS

| 5,629,204 | A | 5/1997 | Honjo et al. |
| 5,698,520 | A | 12/1997 | Honjo et al. |
| 6,596,541 | B2 | 7/2003 | Murphy et al. |
| 6,803,792 | B2 | 10/2004 | Yasuda et al. |
| 6,808,710 | B1 | 10/2004 | Wood et al. |
| 6,936,704 | B1 | 8/2005 | Freeman et al. |
| 7,029,674 | B2 | 4/2006 | Carreno et al. |
| 7,038,013 | B2 | 5/2006 | Freeman et al. |
| 7,087,411 | B2 | 8/2006 | Daly et al. |
| 7,101,550 | B2 | 9/2006 | Wood et al. |
| 7,488,802 | B2 | 2/2009 | Collins et al. |
| 7,521,051 | B2 | 4/2009 | Collins et al. |
| 7,563,869 | B2 | 7/2009 | Honjo et al. |
| 7,595,048 | B2 | 9/2009 | Honjo et al. |
| 7,635,757 | B2 | 12/2009 | Freeman et al. |
| 7,638,492 | B2 | 12/2009 | Wood et al. |
| 7,709,214 | B2 | 5/2010 | Freeman et al. |
| 7,722,868 | B2 | 5/2010 | Freeman et al. |
| 7,794,710 | B2 | 9/2010 | Chen et al. |
| 7,943,742 | B2 | 5/2011 | Violette et al. |
| 7,943,743 | B2 | 5/2011 | Korman et al. |
| 7,998,479 | B2 | 8/2011 | Honjo et al. |
| 8,008,449 | B2 | 8/2011 | Korman et al. |
| 8,088,905 | B2 | 1/2012 | Collins et al. |
| 8,168,179 | B2 | 5/2012 | Honjo et al. |
| 8,168,757 | B2 | 5/2012 | Finnefrock et al. |
| 8,216,996 | B2 | 7/2012 | Minato et al. |
| 8,217,149 | B2 | 7/2012 | Irving et al. |
| 8,246,955 | B2 | 8/2012 | Honjo et al. |
| 8,246,995 | B2 | 8/2012 | Dai et al. |
| 8,257,740 | B1 | 9/2012 | Sung et al. |
| 8,287,856 | B2 | 10/2012 | Li et al. |
| 8,354,509 | B2 | 1/2013 | Carven et al. |

(Continued)

FOREIGN PATENT DOCUMENTS

| CN | 101213297 A | 7/2008 |
| EA | 201490369 A1 | 8/2014 |

(Continued)

OTHER PUBLICATIONS

Stanglmaier et al. (Int. J, Cancer, 123, 1181-1189, 2008, in IDS from Mar. 24, 2021).*

(Continued)

*Primary Examiner* — Nelson B Moseley, II

(74) *Attorney, Agent, or Firm* — Fox Rothschild LLP; Aparna G. Patankar

(57) ABSTRACT

The present invention provides methods for treating, reducing the severity, or inhibiting the growth of cancer (e.g., a B-cell cancer such as Hodgkin's lymphoma or acute lymphoblastic leukemia). The methods of the present invention comprise administering to a subject in need thereof a therapeutically effective amount of an antibody or antigen-binding fragment thereof that specifically binds to programmed death 1 (PD-1) receptor in combination with a therapeutically effective amount of a bispecific antibody that specifically binds to CD20 and CD3.

33 Claims, 9 Drawing Sheets

Specification includes a Sequence Listing.

(56) References Cited

U.S. PATENT DOCUMENTS

| | | |
|---|---|---|
| 8,383,796 B2 | 2/2013 | Korman et al. |
| 8,460,927 B2 | 6/2013 | Chen |
| 8,552,154 B2 | 10/2013 | Freeman et al. |
| 8,574,872 B2 | 11/2013 | Minato et al. |
| 8,580,247 B2 | 11/2013 | Li et al. |
| 8,617,546 B2 | 12/2013 | Kang et al. |
| 8,709,416 B2 | 4/2014 | Langermann et al. |
| 8,728,474 B2 | 5/2014 | Honjo et al. |
| 8,741,295 B2 | 6/2014 | Olive |
| 8,779,105 B2 | 7/2014 | Korman et al. |
| 8,779,108 B2 | 7/2014 | Queva et al. |
| 9,359,437 B2 | 6/2016 | Davis et al. |
| 9,657,102 B2 | 5/2017 | Smith et al. |
| 9,987,500 B2 | 6/2018 | Papadopoulos et al. |
| 10,143,186 B2 | 12/2018 | McWhirter et al. |
| 10,736,976 B2 | 8/2020 | Kelly et al. |
| 10,737,113 B2 | 8/2020 | Papadopoulos et al. |
| 11,117,970 B2 | 9/2021 | Papadopoulos et al. |
| 2004/0101920 A1 | 5/2004 | Radziejewski et al. |
| 2005/0226876 A1 | 10/2005 | Graus et al. |
| 2005/0244403 A1 | 11/2005 | Lazar et al. |
| 2007/0280945 A1 | 12/2007 | Stevens et al. |
| 2009/0055944 A1 | 2/2009 | Korman et al. |
| 2009/0217401 A1 | 8/2009 | Korman et al. |
| 2009/0274666 A1 | 11/2009 | Chen |
| 2009/0317368 A1 | 12/2009 | Chen |
| 2010/0203056 A1 | 8/2010 | Irving et al. |
| 2010/0331527 A1 | 12/2010 | Davis et al. |
| 2011/0008369 A1 | 1/2011 | Finnefrock et al. |
| 2011/0171215 A1 | 7/2011 | Davis et al. |
| 2011/0171220 A1 | 7/2011 | Davis |
| 2011/0177088 A1 | 7/2011 | Olive et al. |
| 2011/0195454 A1 | 8/2011 | McWhirter et al. |
| 2012/0027759 A1 | 2/2012 | Chen et al. |
| 2012/0121634 A1 | 5/2012 | Chen et al. |
| 2013/0017199 A1 | 1/2013 | Langermann |
| 2013/0022595 A1 | 1/2013 | Rotem-Yehudar et al. |
| 2013/0034559 A1 | 2/2013 | Queva et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0095098 A1 | 4/2013 | Tyson |
| 2013/0108651 A1 | 5/2013 | Carven et al. |
| 2013/0109843 A1 | 5/2013 | Carven et al. |
| 2013/0122014 A1 | 5/2013 | Korman et al. |
| 2013/0164294 A1 | 6/2013 | Honjo et al. |
| 2013/0247234 A1 | 9/2013 | McWhirter et al. |
| 2013/0291136 A1 | 10/2013 | Freeman et al. |
| 2013/0303250 A1 | 11/2013 | Moore |
| 2014/0088295 A1 | 3/2014 | Smith et al. |
| 2014/0212422 A1 | 7/2014 | Korman et al. |
| 2014/0243504 A1 | 8/2014 | Davis et al. |
| 2014/0271684 A1 | 9/2014 | Li et al. |
| 2014/0308299 A1 | 10/2014 | Allison et al. |
| 2015/0166661 A1 | 6/2015 | Chen et al. |
| 2015/0203579 A1* | 7/2015 | Papadopoulos ......... A61P 29/00 600/1 |
| 2015/0266966 A1* | 9/2015 | Smith .................... A61P 17/00 530/387.3 |
| 2016/0311903 A1 | 10/2016 | West et al. |
| 2017/0008951 A1 | 1/2017 | Block et al. |
| 2017/0044259 A1 | 2/2017 | Tipton et al. |
| 2017/0174779 A1 | 6/2017 | Varghese et al. |
| 2019/0040137 A1 | 2/2019 | Hu et al. |
| 2020/0283518 A1 | 9/2020 | Liot et al. |
| 2021/0388091 A1 | 12/2021 | Fury et al. |
| 2022/0184241 A1 | 6/2022 | Kelly et al. |
| 2022/0259313 A1 | 8/2022 | Fury et al. |

FOREIGN PATENT DOCUMENTS

| | | |
|---|---|---|
| EP | 0670369 A2 | 9/1995 |
| EP | 1591527 A1 | 11/2005 |
| EP | 1210424 B1 | 2/2007 |
| EP | 2161336 A1 | 3/2010 |
| EP | 2172219 A1 | 4/2010 |
| EP | 2206517 A1 | 7/2010 |
| EP | 1537878 B1 | 9/2010 |
| EP | 2262837 A2 | 12/2010 |
| EP | 1576014 B1 | 6/2011 |
| EP | 2418278 A2 | 2/2012 |
| EP | 2468765 A1 | 6/2012 |
| EP | 2500353 A2 | 9/2012 |
| EP | 2504028 A2 | 10/2012 |
| EP | 2535354 A1 | 12/2012 |
| EP | 1297135 B1 | 1/2013 |
| JP | 2006-340714 A | 12/2006 |
| WO | 99/058572 A1 | 11/1999 |
| WO | 2001039722 A2 | 6/2001 |
| WO | 2002078731 A1 | 10/2002 |
| WO | 2003042402 A2 | 5/2003 |
| WO | 2004056875 | 7/2004 |
| WO | 2004056875 A1 | 7/2004 |
| WO | 2005103081 | 11/2005 |
| WO | 2005103081 A2 | 11/2005 |
| WO | 2006121168 | 11/2006 |
| WO | 2006121168 A1 | 11/2006 |
| WO | 2007002223 | 1/2007 |
| WO | 2007002223 A2 | 1/2007 |
| WO | 2007005874 | 1/2007 |
| WO | 2007005874 A2 | 1/2007 |
| WO | 2007/093630 A1 | 8/2007 |
| WO | 2008156712 | 12/2008 |
| WO | 09/018411 A1 | 2/2009 |
| WO | 2009024531 | 2/2009 |
| WO | 2009024531 A1 | 2/2009 |
| WO | 2009030285 A1 | 3/2009 |
| WO | 2009101611 | 8/2009 |
| WO | 2009101611 A1 | 8/2009 |
| WO | 2009/114335 A2 | 9/2009 |
| WO | 2009114335 | 9/2009 |
| WO | 2010027423 A2 | 3/2010 |
| WO | 2010029434 | 3/2010 |
| WO | 2010029434 A1 | 3/2010 |
| WO | 2010029435 | 3/2010 |
| WO | 2010029435 A1 | 3/2010 |
| WO | 2010036959 | 4/2010 |
| WO | 2010036959 A2 | 4/2010 |
| WO | 2010077634 | 7/2010 |
| WO | 2010077634 A1 | 7/2010 |
| WO | 2010/089411 A2 | 8/2010 |
| WO | 2010089411 | 8/2010 |
| WO | 2011/066342 A2 | 6/2011 |
| WO | 2011/066389 A1 | 6/2011 |
| WO | 2011066342 | 6/2011 |
| WO | 2011066389 | 6/2011 |
| WO | 2011/110621 A1 | 9/2011 |
| WO | 2011110604 | 9/2011 |
| WO | 2011110604 A1 | 9/2011 |
| WO | 2011110621 | 9/2011 |
| WO | 2011159877 A2 | 12/2011 |
| WO | 2012145493 | 10/2012 |
| WO | 2012145493 A1 | 10/2012 |
| WO | 2013014668 | 1/2013 |
| WO | 2013014668 A1 | 1/2013 |
| WO | 2013019906 | 2/2013 |
| WO | 2013019906 A1 | 2/2013 |
| WO | 2013079174 | 6/2013 |
| WO | 2013079174 A1 | 6/2013 |
| WO | 2013079945 | 6/2013 |
| WO | 2013079945 A1 | 6/2013 |
| WO | 2013166500 | 11/2013 |
| WO | 2013166500 A1 | 11/2013 |
| WO | 2013169693 | 11/2013 |
| WO | 2013169693 A1 | 11/2013 |
| WO | 2013173223 | 11/2013 |
| WO | 2013173223 A1 | 11/2013 |
| WO | 2013/181452 A1 | 12/2013 |
| WO | 2013181452 | 12/2013 |
| WO | 2014055648 | 4/2014 |
| WO | 2014055648 A1 | 4/2014 |
| WO | 2014066834 | 5/2014 |
| WO | 2014066834 A1 | 5/2014 |

(56) References Cited

FOREIGN PATENT DOCUMENTS

| WO | 2014127917 | 8/2014 |
|---|---|---|
| WO | 2014127917 A1 | 8/2014 |
| WO | 2014151006 | 9/2014 |
| WO | 2014151006 A2 | 9/2014 |
| WO | 2014159562 | 10/2014 |
| WO | 2014159562 A1 | 10/2014 |
| WO | 2014179664 | 11/2014 |
| WO | 2014179664 A2 | 11/2014 |
| WO | 2014194293 | 12/2014 |
| WO | 2014194293 A1 | 12/2014 |
| WO | 2014209804 | 12/2014 |
| WO | 2014209804 A1 | 12/2014 |
| WO | 2015009856 | 1/2015 |
| WO | 2015009856 A2 | 1/2015 |
| WO | 2015/026634 A1 | 2/2015 |
| WO | 2015016718 | 2/2015 |
| WO | 2015016718 A1 | 2/2015 |
| WO | 2015026634 | 2/2015 |
| WO | 2015026684 | 2/2015 |
| WO | 2015026684 A1 | 2/2015 |
| WO | 2015042246 | 3/2015 |
| WO | 2015042246 A1 | 3/2015 |
| WO | 2015048312 | 4/2015 |
| WO | 2015048312 A1 | 4/2015 |
| WO | 2015048520 A1 | 4/2015 |
| WO | 2015095392 A1 | 6/2015 |
| WO | 2015112800 | 7/2015 |
| WO | 2015112800 A1 | 7/2015 |
| WO | 2015112900 A1 | 7/2015 |
| WO | 2015176033 A1 | 11/2015 |
| WO | 2015193352 | 12/2015 |
| WO | 2015193352 A1 | 12/2015 |
| WO | 2015200119 A1 | 12/2015 |
| WO | 2016061142 A1 | 4/2016 |
| WO | 2016191751 A1 | 12/2016 |
| WO | 2008156712 A1 | 8/2017 |

OTHER PUBLICATIONS

Goy et al., "Treatment results of brachytherapy vs. external beam radioation therapy for intermediate-risk prostate cancer with 10-year followup", Brachytherapy (2016), 15(6):687-94.
Burova et al., "Characterization of the Anti-PD-1 Antibody REGN2810 and Its Antitumor Activity in Human PD-1 Knock-In Mice", Col. Cancer Ther. (2017), 16(5):861-70.
Sanders et al., "Challenges to Successful Imprementation of the Immune Checkpoint Inhibitors for Treatment of Glioblastoma", Int. J. Mol. Sci. (2020), 21(8):2759 (pp. 1-18).
Mukherjee et al., "Mouse models of radiation-induced glioblastoma", Oncoscience (2015), 2(12):934-35.
"Clinical Trials Register: A Phase 1 Study to Access Safety and Tolerability of REGN1979, an anti-CD20 x anti-CD3 bispecific monoclonal antibody, and REGN2810, an anti-programmed death-1 (PD-1) monoclonal antibody, in Patients with B-cellMalignancies", EU Clinical Trials Register, https://www.clinicaltrialsregister.eu/ctr-search/trial/2015-001-697-17/ES, 8 pages (Oct. 15, 2015).
"ESMO 2014: Results of a Phase III Randomised Study of Nivolumab in Patients with Advanced Melanoma After Prior Anti-CTLA4 Therapy", European Society for Medical Oncology (2014).
Study of REGN2810 and REGN1979 in Patients With Lymphoma or Acute Lymphoblastic Leukemia | Smart Patients; (Nov. 1, 2015) at https://www.smartpatients.com/trials/NCT02651662.
"Study of REGN2810 and REGN1979 in Patients with Lymphoma or Acute Lymphoblastic Leukemia," retrieved from the internet: https://apifiveclinicaltrials.com/trialpage?dcn=10963&city=Baltimore&coun-try=UnitedStates&start=20&state=Maryland&conditions=lymphoma&id= 207048402254, 1 page (last updated Nov. 16, 2016).
A Phase 1 Study to Access Safety and Tolerability of REGN1979, an anti-CD20 x anti-CD3 bispecific monoclonal antibody, and REGN2810, an anti-programmed death-1 (PD-1) monoclonal antibody, EU Clinical Trials Register, <https://www.clinicaltrialsregister.eu/ctr-search/search?query=2015-001697-17,> 3 pages (Start Date: Dec. 1, 2015).
Study of REGN2810 and REGN1979 in Patients with Lymphoma or Acute Lymphoblastic Leukemia, Smart Patients, <https://www.smartpatients.com/trials/NCT02651662,> 3 pages (Start Date: Nov. 2015).
Ahmed et al., "Clinical outcomes of melanoma brain metastases treated with stereotactic radiation and anti-PD-1 therapy", Annals of Oncology 27, 3: 434-441 (2015).
Al-Lazikani et al., "Standard Conformations for the Canonical Structures of Immunoglobulins," J. Mol. Biol., (1997), 273:. 927-948.
Altschul et al., "Basic Local Alignment Search Tool," J. Mol. Biol., (1990), 215: 403-410.
Altschul et al., "Gapped BLAST and PSI-BLAST: a new generation of protein database search programs," Nucleic Acids Research, (1997), 25(17): 3389-3402.
Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients withB-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES&- gt;].
Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials.com/trialpage?dcn=10963&city=Baltimore-&country=UnitedStates&start=20&state=Maryland&conditions=lymphoma&id=20704-8402254>].
Anonymous, NCT02760498: A Phase 2 Study of REGN2810, a Fully Human Monoclonal Antibody to Programmed Death-1 (PD-1), in Patients With Advanced Cutaneous Squamous Cell Carcinoma, ClinicalTrials.gov rchive,https://clinicaltrials.gov/archive/NCT02760498/2016_05_02 (2016).
Anonymous, Safety, activity, and immune correlates of anti-PD-1 antibody in cancer, <https://clinicaltrials.gov/archive/>NCT02383212/2016_05_02 (2016).
Arruebo et al., "Antibody-Conjugated Nanoparticles for Biomedical Applications," Journal of Nanomaterials, vol. 2009, Article ID 439389, 24 pages, doi:10.1155/2009/439389.
Badoual et al., "PD-1-Expressing Tumor-Infiltrating T Cells are a Favorable Prognostic Biomarker in HPV-Associated Head and Neck Cancer," Cancer Research, (Jan. 1, 2013), 73(1): 128-138.
Bernstein et al., "Immunotherapy and stereotactic ablative radiotherapy (ISABR): a curative approach?", Nature Reviews, Clinical Oncology, (2016) 3:516-524.
Borradori et al., "Rescue therapy with anti-programmed cell death protein 1 inhibitors (PD-1) of advanced cutaneous squamous cell carcinoma and basosquamous carcinoma: preliminary experience in 5 cases," Br J Dermatol., (2016), 175(6):1382-1386.
Brahmer et al., "Safety and Activity of Anti-PD-L1 Antibody in Patients with Advanced Cancer," The New England Journal of Medicine, (Jun. 28, 2012), 366(26): 2455-2465.
Brusa et al., "The PD-1/PD-L1 axis contributes to T cell dysfunction in chronic lymphocytic leukemia," Haematologica 2012 [Epub ahead of print), 48 pages (2012).
Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www.translational-medicine.com/content/11/1/1160>].
Chang et al., "A Case Report of Unresectable Cutaneous Squamous Cell Carcinoma Responsive to Pembrolizumab, a Programmed Cell Death Protein 1 Inhibitor," JAMA Dermatology, Letters: E1-E3 (2015).
Chattopadhyay, "Sequence, structure, function, immunity: structural genomics of costimulation," Immunol. Rev., (May 2009), 229(1): 356-386.

(56) References Cited

OTHER PUBLICATIONS

Chen et al,. "Molecular Pathways: Next-Generation Immunotherapy-Inhibiting Programmed Death-Ligand 1 and Programmed Death-1," Clinical Cancer Research, (Dec. 15, 2012), 18(24): 6580-6587, published online Oct. 19, 2012.
Chen et al., "Molecular mechanisms of T cell co-stimulation and co-inhibition," Nature Rev Immunol., (Apr. 2013), 13:227-242, NIH Public Access Author Manuscript; available in PMC Apr. 1, 2014.
Chen et al., "Molecular mechanisms of T cell co-stimulation and co-inhibition," Nature Rev Immunol., (Apr. 2013), 13:227-242.
Chuang et al., "Regression of a metastatic lung mass after receiving whole brain irradiation: Can the abscopal effect cross the blood-brain barrier?" Asia Pac. J. Clin. Oncol., (Oct. 2018), 14 (5): e548-e550.
Crammer et al., "Treatment of Unresectable and Metastatic Cutaneous Squamous Cell Carcinoma," The Oncologist, (2010), 15:1320-1328.
Crittenden et al., "Current Clinical Trials Testing Combinations of Immunotherapy and Radiation," Seminars in Radiation Oncology, (2015), 25:54-64.
D'Souza et al., "Combining Radiation Therapy with Immune Checkpoint Blockade for Central Nervous System Malignancies", Frontiers in Oncology, (Oct. 7, 2016), 6(212): 1-8.
Da Silva, R. "Anti-PD-1 monoclonal antibody Cancer immunotheraphy," Drugs of the future, (2014), 39(1): 15-24.
Demaria et al., "Immune-Mediated Inhibition of Metastases after Treatment with Local Radiation and CTLA-4 Blockade in a Mouse Model of Breast Cancer," Clinical Cancer Research, (2005), 11:728-734.
Demaria et al., "Ionizing Radiation Inhibition of Distant Untreated Tumors (Abscopal Effect) is Immune Mediated," Int. J. Radiation Oncology Biol. Phys., (2004), 58(3):862-870.
Deng et al., "Irradiation and anti-PD-L1 treatment synergistically promote antitumor immunity in mice," The Journal of Clinical Investigation, (2014), 124(2):687-695.
Dewan et al., "Fractionated but Not Single-Dose Radiotherapy Induces an Immune-Mediated Abscopal Effect when Combined with Anti-CTLA-4 Antibody," Clin. Cancer Res., (2009), 15(17):5379-5388.
Dong et al., "B7-H1, a third member of the B7 family, co-stimulates T-cell proliferation and interleukin-10 secretion," Nature Medicine, (Dec. 1999), 5(12): 1365-1369.
Dovedi et al., "Acquired Resistance to Franctionated Radiotherapy Can be Overcome by Concurrent PD-L1 Blockade", Cancer Res. (Oct. 2014) 74 (19); 5458-68.
Eggermont et al., "Smart therapeutic strategies in immune-oncology," Nat. Rev. Clin. Oncol., Advance Online Publication, (Mar. 4, 2014), pp. 1-2.
Ehring, "Hydrogen Exchange/Electrospray Ionization Mass Spectrometry Studies of Structural Features of Proteins and Protein/Protein Interactions," Analytical Biochemistry, (1999), 267: 252-259.
Eisenhauer et al., "New response evaluation criteria in solid tumours: Revised RECIST guideline (version 1.1)," European Journal of Cancer, (2009), 45: 228-247.
Engen et al., "Investigating protein structure and dynamics by hydrogen exchange MS," Analytical Chemistry, (May 1, 2001), 73(9): 256A-265A.
Extended European Search Report issued Feb. 11, 2019 in European Patent Application No. 18206830.4.
Falchook et al., "Responses of metastatic basal cell and cutaneous squamous cell carcinomas to anti-PD1 monoclonal antibody REGN2810," J Immunother Cancer, (2016), 4(70):1-5.
Feuchtinger et al., "Leukemia Related Co-Stimulation/Co-Inhibition Predict T-Cell Attack of Acute Lymphoblastic Leukemia Mediated by Blinatumomab," Blood, (2015), 126:3764 (Abstract).
Fife et al., "The role of the PD-1 pathway in autoimmunity and peripheral tolerance," Ann. N.Y. Acad. Sci.,(2011), 1217: 45-59.

Finger et al., "The Human PD-1 Gene: Complete cDNA, Genomic Organization, and Developmentally Regulated Expression in B Cell Progenitors", Gene., (Sep. 15, 1997) 197(1-2): 177-87.
Fisher et al., "Suppressor T Lymphocytes Control the Development of Primary Skin Cancers in Ultraviolet-Irradiated Mice," Science, (1982), 216(4): 1133-1134.
Flies et al., "Blockade of the B7-H1/PD-1 Pathway for Cancer Immunotherapy," Yale Journal of Biology and Medicine, (2011), 84: 409-421.
Francisco et al., "The PD-1 Pathway in Tolerance and Autoimmunity," Immunol. Rev., (Jul. 2010), 236: 219-242.
Freeman et al., "Comparative Immune Phenotypic Analysis of Cutaneous Squamous Cell Carcinoma and Intraepidermal Carcinoma in Immune-Competent Individuals: Proportional Representation of CD8+ T-Cells but Not FoxP3+ Regulatory T-Cells is Associated with Disease Stage," PLOS ONE, (2014), 9(10): e110928:1-9.
Freeman, "Structures of PD-1 with its ligands: Sideways and dancing cheek to cheek," PNAS, (Jul. 29, 2008), 105(30): 10275-10276.
GenBank Accession No. NP_005009 Mar. 15, 2015.
GenBank Accession No. NP_005182 Mar. 15, 2015.
GenBank Accession No. NP_009192 Mar. 15, 2015.
GenBank Accession No. NP_054862 Sep. 25, 2015.
Ghanem et al., "Investigational PD-1 inhibitors for advanced non-small lung cancer: new players in a shifting paradigm", Expert Opin Investig Drugs, (Dec. 2, 2019), 26(12): 1317-19.
Golden et al., "An Abscopal Response to Radiation and Ipilimumab in a Patient with Metastic Non-Small Cell Lung Cancer", Cancer Immunol. Res. (Dec. 2013); 1(6); 365-72.
Golden et al., "Local radiotherapy and granulocyte-macrophage colony-stimulating factor to generate abscopal responses in patients with metastatic solid tumours: a proof-of-principle trial", Lancet Oncol., (2015), 16:795-803.
Gonnet et al., "Exhaustive Matching of the Entire Protein Sequence Database," Science, (Jun. 5, 1992), 256: 1443-1445.
Grimaldi et al., "Abscopal Effects of Radiotherapy on Advanced Melanoma Patients Who Progressed After Ipilimumab Immunotherpy", OncoImmunology, (May 14, 2014) 3(5); e28780; pp. 1-10.
Hamid et al., "Anti-programmed death-1 and anti-programmed death-ligand 1 antibodies in cancer therapy," Expert Opin. Biol. Ther. [Early Online], (Copyright 2013), pp. 1-15.
Herbst et al., "Predictive correlates of response to the anti-PD-L1 antibody MPDL3280A in cancer patients," Nature, (Nov. 27, 2014), 515: 563-567.
Hochleitner et al. "Characterization of a discontinuous epitope of the human immunodeficiency virus (HIV) core protein p24 by epitope excision and differential chemical modification followed by mass spectrometric peptide mapping analysis," Protein Science, (2000), 9: 487-496.
Hofmeyer et al., "The PD-1/PD-L1 (B7-H1) Pathway in Chronic Infection-Induced Cytotoxic T Lymphocyte Exhaustion," Journal of Biomedicine and Biotechnology, (Copyright 2011), vol. 2011, Article ID 451694, 9 pages, doi:10.1155/2011/451694.
Hu et al. "The Abscopal Effect of Radiation Therapy: What is it and How Can We Use it in Breast Cancer?", Curr. Breast Cancer Rep. 2017; 9 (1): 45-51.
International Search Report and Written Opinion for Application No. PCT/US2015/012589 mailed dated Jul. 10, 2015.
International Search Report and Written Opinion for Application No. PCT/US2015/012595 mailed Apr. 14, 2015.
International Search Report and Written Opinion for PCT/US20161068030 (dated May 26, 2017).
International Search Report for PCT/US2017/032397, dated Jul. 11, 2017.
International Search Report for PCT/US2017/032408, dated Jul. 6, 2017.
Wai, et al: "Involvement of PD-L1 on Tumor Cells in the Escape from Host Immune System and Tumor Immunotherapy by PD-L1 Blockade", PNAS, (Sep. 17, 2002), 99(19): 12293-12297.
Brahmer et al: "Phase I Study of Single-Agent Anti-Programmed Death-1 (MDX-1106) in Refractory Solid Tumors: Safety, Clinical

(56) References Cited

OTHER PUBLICATIONS

Activity, Pharmacodynamics, and Immunologic Correlates", Journal of Clinical Oncology, (Jun. 1, 2010), 28(19): 3167-3175.
Jacobs et al., "Immune Checkpoint Modulation in Colorectal Cancer: What's New and What to Expect", J. Immunol. Res., (2015) 158038: 1-16.
Jegache et al., "Major response to pembrolizumab in two patients with locally advanced cutaneous squamous cell carcinoma," JEADV, Letter to the Editor: 1-2 (2017).
Junghans et al., "Anti-Tac-H, a Humanized Antibody to the Interleukin 2 Receptor with New Features for Immunotherapy in Malignant and Immune Disorders," Cancer Research, (1990), 50: 1495-1502.
Kabat, "Sequences of Proteins of Immunological Interest," National Institutes of Health, vol. 1, Bethesda, Md. (1991).
Kachikwu et al., "Radiation Enhances Regulatory T Cell Representation," Int. J. Radiation Oncology Biol. Phys., (2011), 81(4):1128-1135.
Kalbasi, "Radiation and immunotherapy: a synergistic combination," The Journal of Clinical Investigation, (2013), 123(7): 2756-2763.
Kaplon et al., "Anitbodies to watch in 2018", MABS, (Jan. 16, 2018), 10(2): 182-203.
Kasagi et al., "PD-1 and Autoimmunity," Critical Reviews.TM. in Immunology, (2011), 31(4): 265-295.
Kazane et al., "Self-Assembled Antibody Multimers through Peptide Nucleic Acid Conjugation," J. Am. Chem. Soc., (2013), 135: 340-346, published Dec. 4, 2012.
Keir et al., "Programmed Death-1 (PD-1):PD-Ligand 1 Interactions Inhibit TCR-Mediated Positive Selection of Thymocytes," The Journal of Immunology, (2005), 175: 7372-7379.
Klein et al., "Progress in overcoming the chain association issue in bispecific heterodimeric IgG antibodies," mAbs, (Nov./Dec. 2012), 4(6): 653-663.
Kufer et al., "A revival of bispecific antibodies," TRENDS in Biotechnology, (May 2004), 22(5): 238-244.
Langer, "New Methods of Drug Delivery," Science, (Sep. 28, 1990), 249: 1527-1533.
Lin et al., "The PD-1/PD-L1 complex resembles the antigen-binding Fv domains of antibodies and T cell receptors," PNAS, (Feb. 26, 2008), 105(8): 3011-3016.
Liniker et al., Safety and Activity of Combined Radiation Therapy (RT) and Anti-PD-1 Antibodies (PD-1) in Patients (pts) With Metastatic Melanoma, International Journal of Radiation: Oncology Biology Phsics, (2015), 93(3): E635.
Lipson et al., "Durable Cancer Regression Off-Treatment and Effective Reinduction Therapy with an Anti-PD-1 Antibody," Clinical Cancer Research, (Jan. 15, 2013), 19(2): 462-468.
Lugade et al., "Local Radiation Therapy of B16 Melanoma Tumors Increases the Generation of Tumor Antigen-Specific Effector Cells That Traffic to the Tumor," J. Immunol, (2005), 174:7516-7523.
Mahoney et al, The Next Immune-Checkpoint Inhibitors: PD-1/PD-L1 Blockade in Melanoma, Clinical Therapeutics, (2015), 37(4): 764-782.
Martin et al., "Modeling antibody hypervariable loops: A combined algorithm," Proc. Natl. Acad. Sci. USA, (Dec. 1989), 86: 9268-9272.
Mavropoulos et al., "Prospects for personalized targeted therapies for cutaneous squamous cell carcinoma," Seminars in Cutaneous Medicine and Surgery, (2014), 33:72-75.
McDermott et al., "PD-1 as a potential target in cancer therapy" Cancer Med., (2013), 2(5): 662-673.
Mohiuddin et al., High-Dose Radiation as a Dramatic, Immunological Primer in Locally Advanced Melanoma, CUREUS (2015).
Momtaz et al., Pharmacogenomics and Personalized Medicine, (2014), 7: 357-365.
Muhleisen et al., "Progression of cutaneous squamous cell carcinoma in immunosuppressed patients is associated with reduced CD123+ and FOXP3+ cells in the perineoplastic inflammatory infiltrate," Histopathology, (2009), 55:67-76.

Nagasaka et al., "PD1/PD-L1 inhibition as a potential radiosensitizer in head and neck squamous cell carcinoma: a case report", Journal for Immuno Therapy of Cancer, (2016) 4(83): 1-4.
Nishino et al., "Developing a Common Language for Tumor Response to Immunotherapy: Immune-Related Response Criteria Using Unidimensional Measurements," Clinical Cancer Research, (Jul. 15, 2013), 19(14): 3936.
Office Action for Chilean Patent Application No. 1871-2016 (mailed Feb. 5, 2018).
Office Action issued Jan. 4, 2019 in Malaysian Patent Application No. PI 2016702408.
Tutt et al., "Trispecific F(ab')3 derivatives that use cooperative signaling via the TCR/CD3 complex and CD2 to activate and redirect resting cytotoxic T cells," J. Immunol, (Jul. 1, 1991), 147(1): 60-69.
U.S. Appl. No. 15/593,897, filed May 12, 2017.
U.S. Appl. No. 15/593,915, filed May 12, 2017.
U.S. Appl. No. 15/147,791, Notice of Allowance mailed Mar. 1, 2018.
U.S. Appl. No. 15/147,791, Notice of Allowance mailed Jun. 12, 2018.
U.S. Appl. No. 15/527,002, Requirement for Restriction/Election mailed Aug. 24, 2018.
Vajdos et al., "Comprehensive Functional Maps of the Antigen-binding Site of an Anti-ErbB2 Antibody Obtained with Shotgun Scanning Mutagenesis," J. Mol. Biol., (2002), 320: 415-428.
Vanpouille-Box et al., "TGFß is a Master Regulator of Raiation Therapy-Induced Antitumor Immunity", Cancer Res., (Jun. 1, 2015) 75(11); 2232-42.
Vanpouille-Box, "Towards precision radiotherapy for use with immune checkpoint blockers", Clin. Cancer Res., clincanres.0037.2017 (2017).
Victor et al., "Radiation and dual checkpoint blockade activate non-redundant immune mechanisms in cancer," Nature, (2015), 520(7547):373-377.
Wang et al., "Suppression of type I IFN signaling in tumors mediates resistance to anti-PD-1 treatment that can be overcome by radiotherapy", Cancer Res., (2016), 77(4): 839-850.
Wang et al., "PD-1/PDL1 and CD28/CD80 pathways modulate natural killer T cell function to inhibit hepatitis B virus replication," Journal of Viral Hepatitis, (2013), 20(Suppl. 1): 27-39.
Watanabe et al., "Coinhibitory Molecules in Autoimmune Diseases," Clinical and Developmental Immunology, vol. 2012, Article ID 269756, 7 pages, doi:10.1155/2012/269756.
Weber, "Immune Checkpoint Proteins: A New Therapeutic Paradigm for Cancer—Preclinical Background: CTLA-4 and PD-1 Blockade," Semin Oncol, (2010), 37: 430-439.
Weichselbaum et al., "Radiotherapy and immunotherapy: a beneficial liaison?", Nat Rev Clin Oncol, (2017), 14(6):365-379.
Wu et al., "Targeting the Inhibitory Receptor CTLA-4 on T Cells Increased Abscopal Effects in Murine Mesothelioma Model", Oncotarget, (May 20, 2015) 6 (14): 12468-80.
Wu et al., "Receptor-mediated in Vitro Gene Transformation by a Soluble DNA Carrier System," J. Biol. Chem., (Apr. 5, 1987), 262(10): 4429-4432.
Zeng et al., "Anti-PD-1 Blockade and Stereotactic Radiation Produce Long-Term Survival in Mice with Intracranial Gliomas," International Journal of Radiation Oncology, (2013), 86(2): 1-7.
Zielinski et al., "Rationale for targeting the immune system through checkpoint molecule blockade in the treatment of non-small-cell lung cancer," Annals of Oncology, (May 2013), 24(5): 1170-1179.
Zoran et al., "Programmed death 1 (PD-1) lymphocytes and ligand (PD-L1) in colorectal cancer and their relationship to microsatellite instability status," J Clin Oncol., (2014), 32(5s) (suppl; abstr 3625): 2 pages.
Zou et al., "Inhibitory B7-family molecules in the tumour microenvironment," Nature Reviews|Immunology, (Jun. 2008), 8: 467-477.
Reardon et al., "Glioblastoma Eradication Following Immune Checkpoint Blockade in an Orthotopic, Immunocompetent Model," Cancer Immunol Res (2016), 4(2): 124-35.
Reck, M. et al., "Metatastic non-small-cell lung cancer (NSCLC): ESMO Clinical Practice Guidelines for diagnosis, treatment and follow-up", Annals of Ocology (2014) 25 (Supp. 3): iii27-iii39.

(56) References Cited

OTHER PUBLICATIONS

Borghaei et al., "Nivolumab versus Docetaxel in Advanced Nonsquamous Non-small Cell Lung Cancer", N Engl J Med (2015), 373(17):1627-1639.
Garon et al., "Pembrolizumab for the Treatment of Non-Small-Cell Lung Cancer", N Engl J Med (2015), 372:2018-2028.
Ohaegbulam et al: "Human Cancer Immunotherapy with Antibodies to the PD-1 and PD-L1 Pathway", Trends in Molecular Medicine, (Jan. 2015), 21(1): 24-33.
Opposition for Colombian Patent Application No. NC2016/0000106 (dated May 5, 2017).
Padlan et al., "Identification of specificity-determining residues in antibodies," FASEB J, (Jan. 1995), 9: 133-139.
Papadopoulos et al. "REGN2810, a Human Anti-PD-1 Monoclonal Antibody, for Patients with Unresectable Locally Advanced or Metastatic Cutaneous Squamous Cell Carcinoma (CSCC): Initial Safety and Efficacy," ASCO Annual Meeting (2017).
Papadopoulos et al., "A first-in-human study of REGN2810, a monoclonal, fully human antibody to programmed death-1 (PD-1), in combination with immunomodulators including hypofractionated radiotherapy (hfRT)", J. Clin. Oncol., (May 20, 2016) 34 (15 Suppl.); 3024: 1-5.
Pardoll, "The blockade of immune checkpoints in cancer immunotherapy," Nature Reviews|Cancer, (Apr. 2012), 12:252-264.
Park et al., "PD-1 Restrains Radiotherapy-Induced Abscopal Effect", Cancer Immunol Res, (2015), 3(6):610-619.
Pearson, "Flexible Sequence Similarity Searching with the FASTA3 Program Package," Methods Mol Biol, (2000), 132:185-219.
Pearson, W., "Chapter 26. Using the FASTA Program to Search Protein and DNA Sequence Databases," Methods in Molecular Biology, (1994), vol. 24: Computer Analysis of Sequence Data, Part 1: 307-331.
Peggs et al., "PD-1 blockade: promoting endogenous anti-tumor immunity," Expert Rev. Anticancer Ther., (2012), 12(10): 1279-1282.
Peng, "PD-1 Blockade Enhances T-cell Migration to Tumors by Elevating IFN-.gamma. Inducible Chemokines," Cancer Res., (Published OnlineFirst Aug. 20, 2012), 72(20): 5209-5218.
Pickering et al., "Mutational landscape of aggressive cutaneous squamous cell carcinoma," Clin Cancer Res., (2014), 20 (24):6582-6592.
Postow et al., "Immunologic Correlates of the Abscopal Effect in a Patient with Melanoma," The New England Journal of Medicine, (2012), 366:925-931.
Postow et al., "Nivolumab and Ipilimumab Versus Ipilimumab in Untreated Melanoma", N. Engl. J. Med. (May 21, 2015) 372: 2006-17.
Postow et al., "Targeting Immune Checkpoints: Releasing the Restraints on Anti-tumor Immunity for Patients with Melanoma," Cancer J., (2012), 18(2): 153-159.
Powell et al., "Compendium of Excipients for Parenteral Formulations" PDA Journal of Pharmaceutical & Technology, (Sep.-Oct. 1998), 52(5): 238-311.
Powles et al., "MPDL3280A (anti-PD-L1) treatment leads to clinical activity in metastatic bladder cancer," Nature, (Nov. 27, 2014), 515: 558-562.
Raghuraman et al., "Spontaneous Clearance of Chronic Hepatitis C Virus Infection is Associated with Appearance of Neutralizing Antibodies and Reversal of T-Cell Exhaustion," The Journal of Infectious Diseases, (Mar. 1, 2012), 205: 763-771.
Ramesh Rengan et al., Radiation Therapy Contraindications and Safety Panel: Re-irradiation, Novel Combination Therapies, and Hypofractionation, <https://www.astro.org/uploadedFiles?MAIN_SITE_Meeting_and_Education/Events_(ASTRO)/2016/Sample_ASTRO_Meeting/Content_Pieces/RTPaneCombined.pdf: 31-32 (2016).
Reddy et al., "Elimination of Fc Receptor-Dependent Effector Functions of a Modified IgG4 Monoclonal Antibody to Human CD4," J. Immunol, (2000), 164: 1925-1933.
Reineke, "Antibody Epitope Mapping Using Arrays of Synthetic Peptides," Methods in Molecular Biology, (2004), vol. 248: Antibody Engineering: Methods and Protocols: 443-463.
Rennert, "Last Week's Immune Checkpoint Papers in Nature are Complicated!," SugarCone Biotech, htt://www.sugarconebotech.com/?p=814, (Dec. 4, 2014) pp. 1-4.
Reynders et al., "The abscopal effect of local radiotherapy: using immunotherapy to make a rare event clinically relevant" Cancer Treat Rev. (Jun. 2015), 41(6): 503-10.
Ribas, "Tumor Immunotherapy Directed at PD-1," The New England Journal of Medicine, (Jun. 28, 2012), 366(26): 2517-2519.
Riella et al., "Role of the PD-1 Pathway in the Immune Response," American Journal of Transplantation, (2012), 12: 2575-2587.
Riley, "PD-1 signaling in Primary T cells," Immunol. Rev., (May 2009), 229(1): 114-125.
Rodriguez-Ruiz et al., "Abscopal Effects of Radiotherapy are Enhanced by Combined Immunostimulatory mAbs and are Dependent on CD8 T Cells and Crosspriming", Cancer Res., (2016), 76:5994-6005.
Rudikoff et al., "Single amino acid substitute altering antigen-binding specificity" Proc. Natl. Acad. Sci. USA, (Mar. 1982), 79(6): 1979-83.
Saâda-Bouzid et al., "Hyperprogression during anti-PD-1/PD-L1 therapy in patients with recurrent and/or metastatic head and neck squamous cell carcinoma", Annals of Oncology, (Oct. 7, 2017), 28(7): 1605-11.
Schalper et al., "In situ Tumor PD-L1 mRNA expression is associated with increased TILs and better outcome in breast carcinomas," Clinical Cancer Research, Author Manuscript (Published OnlineFirst on Mar. 19, 2014); DOI:10.1158/1078-0432.CCR-13-2702.
Schaper et al., "The Pattern and Clinicopathological Correlates of PD-L1 Expression in Cutaneous Squamous Cell Carcinoma," Running head: PD-L1 expression in cutaneous squamous cell carcinoma, Research Letter (2016).
Schoenhals et al., "Preclinical Rationale and Clinical Considerations for Radiotherapy Plus Immunotherapy: Going Beyond Local Control", The Cancer Journal, (2016), 22:130-137.
Seyedin et al., "Strategies for Combining Immunotherapy with Radiation for Anticancer Therapy", Immunotherapy, (2015) 7(9): 967-80.
Sharabi et al., "Stereotactic Radiation Therapy Augments Antigen-Specific PD-1 Mediated Anti-Tumor Immune Responses via Cross-Presentation of Tumor Antigen," Cancer Immunol Res, (2014), 3:345-355.
Sheridan, "Cautious optimism surrounds early clinical data for PD-1 blocker," Nature Biotechnology, (Aug. 2012), 30(8): 729-730.
Shetty et al., "PD-1 blockade during chronic SIV infection reduces hyperimmune activation and microbial translocation in rhesus macaques," The Journal of Clinical Investigation, (May 2012), 122(5): 1712-1716.
Shields et al., "Lack of Fucose on Human IgG1 N-Linked Oligosaccharide Improves Binding to Human FcγRIII and Antibody-dependent Cellular Toxicity," J. Biol. Chem., (Jul. 26, 2002), 277(30):26733-26740.
Siiman et al., "Cell Surface Receptor-Antibody Association Constants and Enumeration of Receptor Sites for Monoclonal Antibodies," Cytometry, (2000), 40:316-326.
Slater et al., "PD-L1 expression in cutaneous squamous cell carcinoma correlates with risk of metastasis," Knoxville Dermatopathology Laboratory, J Cutan Path, (2016), 43(8):663-70.
Soura et al., "Programmed cell death protein-1 inhibitors for immunotherapy of advanced nonmelanoma skin cancer: showing early promise," British Journal of Dermatology, (2016), 175(6):1150-1151.
Stanglmaier et al., "Bi20 (FBTA05) a novel trifunctional bispecific antibody (anti-CD20 x anti-CD3), mediates efficient killing of B-cell lymphoma cells even with very low CD20 expression levels", Int. J. Cancer, (2008), 123:1181-1189.
Stevenson et al., "Expression of Programmed Cell Death Ligand in Cutaneous Squamous Cell Carcinoma and Treatment of Locally Advanced Disease With Pembrolizumab," JAMA Dermatol., (2017), 153(4):299-303.

(56) References Cited

OTHER PUBLICATIONS

Sznol et al., "Antagonist Antibodies to PD-1 and B7-H1 (PD-L1) in the Treatment of Advanced Human Cancer," Clinical Cancer Research, (Mar. 1, 2013), 19,(5): 1021-1034.
Third Party Submission Under 37 CFR 1.290 Concise Description of Relevance filed in U.S. Appl. No. 14/603,776 dated Jul. 4, 2016.
Topalian et al., "Safety, Activity, and Immune Correlates of Anti-PD-1 Antibody in Cancer", N Engl J Med, (2012), 366(26): 2443-2454.
Topalian, slides presented at MMS Annual Education Program May 9-11, 2013 in Boston MA.
Topalian et al., "Targeting the PD-1/B7-H1(PD-L1) pathway to activate anti-tumor immunity," Current Opinion in Immunology, (2012), 24:207-212.
Tran et al., "Follow-up on Programmed Cell Death 1 Inhibitor for Cutaneous Squamous Cell Carcinoma," JAMA Dermatology, Letters: E1-E3 (2016).
Tsai et al., Human Vaccines & Immunotherapeutics, (2014), 10: 3111-3116.
Tumeh et al. "PD-1 blockade induces responses by inhibiting adaptive immune resistance," Nature, (Nov. 27, 2014), 515: 568-571.
Baker, "PD-1 inhibition in advanced Merkel-cell carcinoma," The Lancet (Apr. 28, 2016), https://dx.doi.org/10.1016/S1470-2045(16)30112-7.
Wiznia et al., "Treatment of Basal Cell Carcinoma in the Elderly: What Nondermatologists Need to Know," Am J Med, Excerpta Medica, Inc, US (2016), 129(7):655-660.
Murphy et al., "Mice with megabase humanization of their immunoglobulin genes generate antibodies as efficiently as normal mice" PNAS (2014), 111(14): 5153-58.
Kyratsous et al., "Reply to Dimitrov et al.: VelociSuite technologies are a foundation for rapid therapeutic antibody development," PNAS (2015), 112(37): E5116.
Proctor et al., "Vismodegib: An Inhibitor of the Hedgehog Signaling Pathway in the Treatment of Basal Cell Carcinoma", Annals of Pharmacotheraphy (2014), 47(1): 99-106.
Pantelyushin et al., "Cross-Reactivity and Functionality of Approved Human Immune Checkpoint Blockers in Dogs," Cancers (2021), 13(4): 785 (18 pp.).
Pedoeem et al., "Programmed death-1 pathway in cancer and autoimmunity," Clin. Immunol. (2014), 153(1): 145-52.
Blankenstein et al., "The determinants of tumour immunogenicity," Nat. Rev. Cancer (2012), 12(4): 307-13.
Curran et al., "PD-1 and CTLA-4 combination blockade expands infiltrating T cells and reduces regulatory T and myeloid cells within B16 melanoma tumors," Proc. Natl. Acad. Sci. USA (2010), 107(9): 4275-80.
Rodriguez-Ruiz et al., "Brachytherapy attains abscopal effects when combined with immunostimulatory monoclonal antibodies," Brachytherapy (2017), 16: 1246-1521.
Schrörs et al., "MC38 colorectal tumor cell lines from two different sources display substansital differences in transcriptome, mutanome and neoantigen expression," Front. Immunol. (2023), 14: 1102282 (10 pp.).

\* cited by examiner

SEQUENCE LISTING

<160> NUMBER OF SEQ ID NOS: 22

<210> SEQ ID NO 1

```
<211> LENGTH: 117
<212> TYPE: PRT
<213> ORGANISM: Artificial Sequence
<220> FEATURE:
<223> OTHER INFORMATION: anti-PD-1 HCVR

<400> SEQUENCE: 1

Glu Val Gln Leu Leu Glu Ser Gly Gly Val Leu Val Gln Pro Gly Gly
 1               5                  10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: anti-PD-1 LCVR

<400> SEQUENCE: 2

Asp Ile Gln Met Thr Gln Ser Pro Ser Ser Leu Ser Ala Ser Val Gly
 1               5                  10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105

<210> SEQ ID NO 3
<211> LENGTH: 8
<212> TYPE: PRT
<213> ORGANISM: Artificial Sequence
<220> FEATURE:
<223> OTHER INFORMATION: anti-PD-1 HCDR1

<400> SEQUENCE: 3

Gly Phe Thr Phe Ser Asn Phe Gly
 1               5

<210> SEQ ID NO 4
<211> LENGTH: 8
```

```
<212> TYPE: PRT
<213> ORGANISM: Artificial Sequence
<220> FEATURE:
<223> OTHER INFORMATION: anti-PD-1 HCDR2

<400> SEQUENCE: 4

Ile Ser Gly Gly Gly Arg Asp Thr
1               5

<210> SEQ ID NO 5
<211> LENGTH: 10
<212> TYPE: PRT
<213> ORGANISM: Artificial Sequence
<220> FEATURE:
<223> OTHER INFORMATION: anti-PD-1 HCDR3

<400> SEQUENCE: 5

Val Lys Trp Gly Asn Ile Tyr Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: anti-PD-1 LCDR1

<400> SEQUENCE: 6

Leu Ser Ile Asn Thr Phe
1               5

<210> SEQ ID NO 7
<211> LENGTH: 3
<212> TYPE: PRT
<213> ORGANISM: Artificial Sequence
<220> FEATURE:
<223> OTHER INFORMATION: anti-PD-1 LCDR2

<400> SEQUENCE: 7

Ala Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: anti-PD-1 LCDR3

<400> SEQUENCE: 8

Gln Gln Ser Ser Asn Thr Pro Phe Thr
1               5

<210> SEQ ID NO 9
<211> LENGTH: 444
<212> TYPE: PRT
<213> ORGANISM: Artificial Sequence
<220> FEATURE:
<223> OTHER INFORMATION: anti-PD-1 HC
      aa 1-117: Variable region
      aa 118-444: Constant region

<400> SEQUENCE: 9

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30
```

```
Gly Met Thr Trp Val Arg Gln Ala Pro Gly Lys Gly Leu Glu Trp Val
            35                  40                  45

Ser Gly Ile Ser Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440
```

```
<210> SEQ ID NO 10
<211> LENGTH: 214
<212> TYPE: PRT
<213> ORGANISM: Artificial Sequence
<220> FEATURE:
<223> OTHER INFORMATION: anti-PD-1 LC
      aa 1-108: Variable region
      aa 109-214: Constant region

<400> SEQUENCE: 10

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 127
<212> TYPE: PRT
<213> ORGANISM: Artificial Sequence
<220> FEATURE:
<223> OTHER INFORMATION: anti-CD20/anti-CD3 A-HCVR

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Gln Tyr
            100                 105                 110

Gly Met Asp Val Trp Gly Gln Gly Thr Thr Val Thr Val Ser Ser
        115                 120                 125
```

<210> SEQ ID NO 12
<211> LENGTH: 108
<212> TYPE: PRT
<213> ORGANISM: Artificial Sequence
<220> FEATURE:
<223> OTHER INFORMATION: anti-CD20/anti-CD3 LCVR

<400> SEQUENCE: 12

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg
            100                 105
```

<210> SEQ ID NO 13
<211> LENGTH: 123
<212> TYPE: PRT
<213> ORGANISM: Artificial Sequence
<220> FEATURE:
<223> OTHER INFORMATION: anti-CD20/anti-CD3 B-HCVR

<400> SEQUENCE: 13

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Gly Met Asp Val
            100                 105                 110

Trp Gly Gln Gly Thr Thr Val Thr Val Ala Ser
        115                 120
```

<210> SEQ ID NO 14
<211> LENGTH: 8
<212> TYPE: PRT
<213> ORGANISM: Artificial Sequence

```
<220> FEATURE:
<223> OTHER INFORMATION: anti-CD20/anti-CD3 A-HCDR1

<400> SEQUENCE: 14

Gly Phe Thr Phe Asn Asp Tyr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: anti-CD20/anti-CD3 A-HCDR2

<400> SEQUENCE: 15

Ile Ser Trp Asn Ser Asp Ser Ile
1               5

<210> SEQ ID NO 16
<211> LENGTH: 20
<212> TYPE: PRT
<213> ORGANISM: Artificial Sequence
<220> FEATURE:
<223> OTHER INFORMATION: anti-CD20/anti-CD3 A-HCDR3

<400> SEQUENCE: 16

Ala Lys Asp Asn His Tyr Gly Ser Gly Ser Tyr Tyr Tyr Gln Tyr
1               5                   10                  15

Gly Met Asp Val
            20

<210> SEQ ID NO 17
<211> LENGTH: 6
<212> TYPE: PRT
<213> ORGANISM: Artificial Sequence
<220> FEATURE:
<223> OTHER INFORMATION: anti-CD20/anti-CD3 LCDR1

<400> SEQUENCE: 17

Gln Ser Val Ser Ser Asn
1               5

<210> SEQ ID NO 18
<211> LENGTH: 3
<212> TYPE: PRT
<213> ORGANISM: Artificial Sequence
<220> FEATURE:
<223> OTHER INFORMATION: anti-CD20/anti-CD3 LCDR2

<400> SEQUENCE: 18

Gly Ala Ser
1

<210> SEQ ID NO 19
<211> LENGTH: 9
<212> TYPE: PRT
<213> ORGANISM: Artificial Sequence
<220> FEATURE:
<223> OTHER INFORMATION: anti-CD20/anti-CD3 LCDR3

<400> SEQUENCE: 19

Gln His Tyr Ile Asn Trp Pro Leu Thr
1               5

<210> SEQ ID NO 20
<211> LENGTH: 8
```

```
<212> TYPE: PRT
<213> ORGANISM: Artificial Sequence
<220> FEATURE:
<223> OTHER INFORMATION: anti-CD20/anti-CD3 B-HCDR1

<400> SEQUENCE: 20

Gly Phe Thr Phe Asp Asp Tyr Thr
1               5

<210> SEQ ID NO 21
<211> LENGTH: 8
<212> TYPE: PRT
<213> ORGANISM: Artificial Sequence
<220> FEATURE:
<223> OTHER INFORMATION: anti-CD20/anti-CD3 B-HCDR2

<400> SEQUENCE: 21

Ile Ser Trp Asn Ser Gly Ser Ile
1               5

<210> SEQ ID NO 22
<211> LENGTH: 16
<212> TYPE: PRT
<213> ORGANISM: Artificial Sequence
<220> FEATURE:
<223> OTHER INFORMATION: anti-CD20/anti-CD3 B-HCDR3

<400> SEQUENCE: 22

Ala Lys Asp Asn Ser Gly Tyr Gly His Tyr Tyr Tyr Gly Met Asp Val
1               5                   10                  15
```

COMBINATION OF ANTI-PD-1 ANTIBODIES AND BISPECIFIC ANTI-CD20/ANTI-CD3 ANTIBODIES TO TREAT CANCER

CROSS-REFERENCE TO RELATED APPLICATIONS

This application is a continuation of U.S. patent application Ser. No. 15/386,453 filed Dec. 21, 2016, which claims the benefit of priority to U.S. Provisional Patent Application No. 62/270,749 filed Dec. 22, 2015, the disclosures of which are hereby incorporated by reference in their entireties.

SEQUENCE LISTING

The present application includes a Sequence Listing in electronic format as a txt file titled "SEQUENCE-LISTING," which was created on Dec. 21, 2016 and which has a size of 13.7 kilobytes (KB). The contents of txt file "SEQUENCE-LISTING" are incorporated by reference herein.

FIELD OF THE INVENTION

The present invention relates to methods for treating cancer comprising administering to a subject in need thereof a therapeutically effective amount of an antibody that specifically binds to programmed death 1 (PD-1) receptor in combination with a bispecific antibody that binds to CD20 and CD3.

BACKGROUND

B-cell cancers are a group of heterogeneous cancers of the white blood cells known as B-lymphocytes and include leukemias (located in the blood) and lymphomas (located in the lymph nodes). B-cell lymphomas include, but are not limited to, non-Hodgkin's lymphoma (NHL), and Hodgkin's lymphoma (HL). Lymphomas are divided into indolent (slow-growing) or aggressive lymphomas. A common indolent lymphoma is follicular lymphoma, while the most common aggressive lymphoma is diffuse large B-cell lymphoma. B-cell leukemias include, but are not limited to, acute lymphoblastic leukemia, hairy cell leukemia and B-cell chronic lymphocytic leukemia.

Most B-cell cancers express CD20 on the cell surface of mature B cells. Methods for treating cancer by targeting CD20 are known in the art. For example, the chimeric anti-CD20 monoclonal antibody rituximab has been used or suggested for use in treating cancers such as NHL, chronic lymphocytic leukemia (CLL) and small lymphocytic lymphoma (SLL), either as monotherapy but more typically in combination with chemotherapy. Although anti-CD20 tumor targeting strategies have shown great promise in clinical settings, not all patients respond to anti-CD20 therapy, and some patients have been shown to develop resistance to or exhibit incomplete responses to anti-CD20 therapy (e.g., partial depletion of peripheral B-cells), for reasons that are not well understood (but which typically do not include loss of CD20 expression). Some patients relapse with a more aggressive phenotype or chemotherapy-resistant disease. Many patients with aggressive lymphomas have poor prognosis and less than 50% chance of relapse-free survival. The prognosis for patients who relapse or are refractory to therapy remains dismal with median survival after salvage therapy of 2 to 8 months. In addition, high-dose chemotherapy leads to severe adverse side effects. Thus, there is a high unmet need for therapies that are effective, prevent relapse and have less side effects for patients with B-cell cancers.

Programmed death-1 (PD-1) receptor signaling in the tumor microenvironment plays a key role in allowing tumor cells to escape immune surveillance by the host immune system. Blockade of the PD-1 signaling pathway has demonstrated clinical activity in patients with multiple tumor types, and antibody therapeutics that block PD-1 (e.g., nivolumab and pembrolizumab) have been approved for the treatment of metastatic melanoma and metastatic squamous non-small cell lung cancer. Recent data has demonstrated the clinical activity of PD-1 blockade in patients with aggressive NHL and Hodgkin's lymphoma (Lesokhin, et al 2014, Abstract 291, 56th ASH Annual Meeting and Exposition, San Francisco, CA; Ansell et al 2015, N. Engl. J. Med. 372(4):311-9).

CD3 is a homodimeric or heterodimeric antigen expressed on T cells in association with the T cell receptor complex (TCR) and is required for T cell activation. Antibodies against CD3 have been shown to cluster CD3 on T cells, thereby causing T cell activation in a manner similar to the engagement of the TCR by peptide-loaded MHC molecules. Bispecific monoclonal antibodies designed to target both CD20 and CD3 bridge CD20-expressing cells with cytotoxic T cells, resulting in CD20-directed polyclonal T cell killing.

In view of the high unmet need for effective therapies for B-cell malignancies, it might be useful, as shown herein, to combine treatment with an agent to augment T-cell function (e.g., a PD-1 inhibitor such as an anti-PD-1 antibody) along with an agent against a target antigen (a bispecific anti-CD20/anti-CD3 antibody).

BRIEF SUMMARY OF THE INVENTION

According to certain embodiments, the present invention provides methods for treating, ameliorating at least one symptom or indication, or inhibiting the growth of cancer in a subject. The methods according to this aspect of the invention comprise administering a therapeutically effective amount of an antibody or antigen-binding fragment thereof that specifically binds to programmed death 1 (PD-1) in combination with a therapeutically effective amount of a bispecific antibody that specifically binds to CD20 and CD3 to a subject in need thereof.

In certain embodiments of the present invention, methods are provided for treating, ameliorating at least one symptom or indication, or inhibiting the growth of cancer in a subject. In certain embodiments of the present invention, methods are provided for delaying the growth of a tumor or preventing tumor recurrence. The methods, according to this aspect of the invention, comprise sequentially administering one or more doses of a therapeutically effective amount of an antibody or antigen-binding fragment thereof that specifically binds to PD-1 in combination with one or more doses of a therapeutically effective amount of a bispecific antibody that specifically binds to CD20 and CD3 to a subject in need thereof.

In certain embodiments, the cancer or tumor is a heme cell tumor or malignancy. In certain embodiments, the cancer or tumor is a B-cell tumor. In certain embodiments, the B-cell tumor is selected from the group consisting of Hodgkin's lymphoma, non-Hodgkin's lymphoma, follicular lymphoma, small lymphocytic lymphoma, lymphoplasmacytoid lymphoma, marginal zone lymphoma, mantle cell lymphoma, diffuse large B-cell lymphoma, B-cell lymphomas, lymphomatoid granulomatosis, Burkitt's lymphoma, acute lymphoblastic leukemia, hairy cell leukemia, and B cell chronic lymphocytic leukemia.

In certain embodiments, each dose of anti-PD-1 antibody comprises 0.1-20 mg/kg of the subject's body weight. In certain embodiments, each dose of anti-PD-1 antibody comprises 0.3, 1 or 3 mg/kg of the subject's body weight. In certain embodiments, each dose of the anti-PD-1 antibody comprises 50-600 mg.

In certain embodiments, each dose of the bispecific antibody against CD20 and CD3 comprises 0.1-10 mg/kg of the subject's body weight. In certain embodiments, each dose of the bispecific antibody comprises 10-8000 micrograms.

In certain embodiments, each dose of the anti-PD-1 antibody comprises 0.3, 1, 3, or 10 mg/kg of the subject's body weight and each dose of the bispecific antibody comprises 10-3000 micrograms. In certain embodiments, each dose of the anti-PD-1 antibody comprises 1, 3, or 10 mg/kg of the subject's body weight and each dose of the bispecific antibody comprises 100, 300, 1000 or 3000 micrograms. In certain embodiments, each dose of the anti-PD-1 antibody comprises 50-300 mg and each dose of the bispecific antibody comprises 100, 300, 1000 or 3000 micrograms.

In certain embodiments, the methods of the present invention comprise administering a therapeutically effective amount of an anti-PD-1 antibody prior to, concurrent with, or subsequent to a bispecific antibody that specifically binds to CD20 and CD3. In one embodiment, the methods of the present invention comprise administering an anti-PD-1 antibody prior to a bispecific anti-CD20/anti-CD3 antibody.

In certain embodiments, the methods of the present invention comprise administering 0-50 therapeutic doses each of an anti-PD-1 antibody and a bispecific antibody against CD20 and CD3, wherein each dose is administered 0.5-12 weeks after the immediately preceding dose. In certain embodiments, each dose of the anti-PD-1 antibody is administered once a week, once in 2 weeks or once in 4 weeks and each dose of the bispecific antibody is administered once a week, once in 2 weeks or once in 4 weeks. In one embodiment, each dose of the anti-PD-1 antibody is administered once in 2 weeks and each dose of the bispecific antibody is administered once a week.

In certain embodiments, each dose of the bispecific antibody is administered (as split doses) in more than 1 fractions, e.g., as 2 or more fractions within the dosing period.

In certain embodiments, the anti-PD-1 antibody and the bispecific antibody are administered in combination with a third therapeutic agent or therapy.

According to certain embodiments, the anti-PD-1 antibody or antigen-binding protein comprises the heavy chain complementarity determining regions (HCDRs) of a heavy chain variable region (HCVR) comprising the amino acid sequence of SEQ ID NO: 1 and the light chain CDRs of a light chain variable region (LCVR) comprising the amino acid sequence of SEQ ID NO: 2. One such type of antigen-binding protein that can be used in the context of the methods of the present invention is an anti-PD-1 antibody such as REGN2810.

According to certain embodiments, the bispecific antibody that binds to CD20 and CD3 comprises: (i) a first antigen-binding arm comprising the heavy chain CDRs (A-HCDR1, A-HCDR1 and A-HCDR3) of a HCVR (A-HCVR) of SEQ ID NO: 11 and the light chain CDRs (LCDR1, LCDR2 and LCDR3) of a LCVR of SEQ ID NO: 12; and (ii) a second antigen-binding arm comprising the heavy chain CDRs (B-HCDR1, B-HCDR2 and B-HCDR3) of a HCVR (B-HCVR) of SEQ ID NO: 13 and the light chain CDRs (LCDR1, LCDR2 and LCDR3) of a LCVR of SEQ ID NO: 12.

In certain embodiments, the present invention provides use of an anti-PD-1 antibody or antigen-binding fragment thereof alone or in combination with a bispecific antibody against CD20 and CD3 in the manufacture of a medicament to treat or inhibit the growth of cancer in a subject, including humans. In certain embodiments, the cancer is a B-cell cancer. In one embodiment, the cancer is non-Hodgkin's lymphoma. In one embodiment, the cancer is Hodgkin's lymphoma. In one embodiment, the cancer is acute lymphoblastic leukemia.

Other embodiments of the present invention will become apparent from a review of the ensuing detailed description.

DETAILED DESCRIPTION

Figure 1:
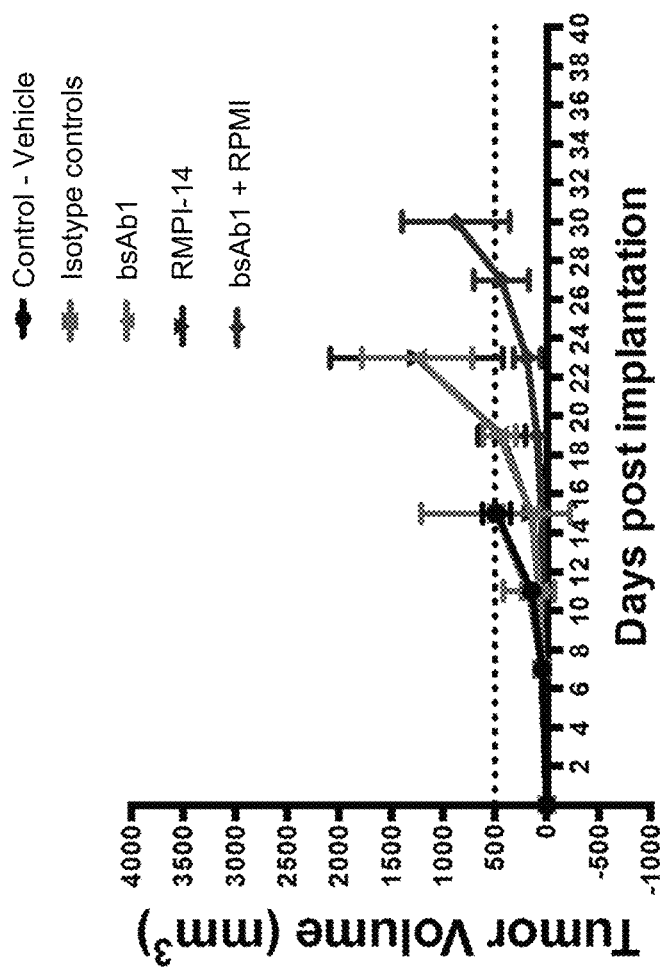
FIG. 1 summarizes the results of in vivo efficacy of anti-mouse PD-1 antibody alone and in combination with bispecific anti-CD20/anti-CD3 antibody against established B16_CD20+ tumors (described in Example 1 herein).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating or Inhibiting the Growth of B-Cell Cancers

The present invention includes methods for treating, ameliorating or reducing the severity of at least one symptom or indication, or inhibiting the growth of a cancer in a subject. The methods according to this aspect of the invention comprise administering a therapeutically effective amount of an antibody or antigen-binding fragment thereof that specifically binds PD-1 in combination with a therapeutically effective amount of a bispecific antibody against CD20 and CD3 to a subject in need thereof. As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, and/or to increase duration of survival of the subject.

As used herein, the expression "a subject in need thereof" means a human or non-human mammal that exhibits one or more symptoms or indications of cancer, and/or who has been diagnosed with cancer, including a B-cell cancer and who needs treatment for the same. In many embodiments, the term "subject" may be interchangeably used with the term "patient". For example, a human subject may be diagnosed with a primary or a metastatic tumor and/or with one or more symptoms or indications including, but not limited to, enlarged lymph node(s), swollen abdomen, chest pain/pressure, unexplained weight loss, fever, night sweats, persistent fatigue, loss of appetite, enlargement of spleen, itching. The expression includes subjects with primary or established B-cell tumors. In specific embodiments, the expression includes human subjects that have and need treatment for a B-cell malignancy, e.g., Hodgkin's lymphoma, non-Hodgkin's lymphoma, follicular lymphoma, small lymphocytic lymphoma, lymphoplasmacytoid lymphoma, marginal zone lymphoma, mantle cell lymphoma, diffuse large B-cell lymphoma, B-cell lymphomas, lymphomatoid granulomatosis, Burkitt's lymphoma, acute lymphoblastic leukemia, hairy cell leukemia, and B cell chronic lymphocytic leukemia. In a further embodiment, the expression includes persons with a pathologic subtype of a B-cell cancer as listed in Tables 3-5 herein. In other specific embodiments, the expression includes subjects with CD20+ tumors (e.g., a tumor with CD20 expression as determined by flow cytometry on ≥20% of leukemic lymphoblasts). In certain embodiments, the expression "a subject in need thereof" includes patients with a B-cell cancer that is resistant to or refractory to or is inadequately controlled by prior therapy (e.g., treatment with a conventional anti-cancer agent). For example, the expression includes subjects who have been treated with a CD20 inhibitor (e.g., rituximab), chemotherapy, or an immune-modulating agent such as a blocker of CTLA, IBB, LAG3 or OX-40. The expression also includes subjects with a B-cell malignancy for which conventional anti-cancer therapy is inadvisable, for example, due to toxic side effects. For example, the expression includes patients who have received one or more cycles of chemotherapy with toxic side effects. In certain embodiments, the expression "a subject in need thereof" includes patients with a B-cell malignancy which has been treated but which has subsequently relapsed or metastasized. For example, patients with a B-cell malignancy that may have received treatment with one or more anti-cancer agents leading to tumor regression; however, subsequently have relapsed with cancer resistant to the one or more anti-cancer agents (e.g., chemotherapy-resistant cancer) are treated with the methods of the present invention.

The expression "a subject in need thereof" also includes subjects who are at risk of developing a B-cell cancer, e.g., persons with a family history of lymphoma, persons with a past history of Epstein-Barr infections such as infectious mononucleosis, or persons with an immune system compromised due to HIV infection or due to immunosuppressive medications.

In certain embodiments, the methods of the present invention may be used to treat patients that show elevated levels of one or more cancer-associated biomarkers [e.g., programmed death ligand 1 (PD-L1), CD20, beta-2-microglobulin, lactate dehydrogenase, BCR-ABL fusion gene, ALK gene rearrangement]. For example, the methods of the present invention comprise administering a therapeutically effective amount of an anti-PD-1 antibody in combination with a bispecific anti-CD20/anti-CD3 antibody to a patient with an elevated level of PD-L1 and/or CD20.

In certain embodiments, the methods of the present invention are used in a subject with a B-cell cancer. The terms "tumor", "cancer" and "malignancy" are interchangeably used herein. The term "B-cell cancer", as used herein, refers to tumors of white blood cells known as B-lymphocytes and includes leukemias (located in the blood) and lymphomas (located in the lymph nodes). The present invention includes methods to treat both leukemias and lymphomas. In certain embodiments, B-cell cancer includes, but is not limited to, Hodgkin's lymphoma, non-Hodgkin's lymphoma, follicular lymphoma, small lymphocytic lymphoma, lymphoplasmacytoid lymphoma, marginal zone lymphoma, mantle cell lymphoma, diffuse large B-cell lymphoma, B-cell lymphomas, lymphomatoid granulomatosis, Burkitt's lymphoma, acute lymphoblastic leukemia, hairy cell leukemia, B cell chronic lymphocytic leukemia, as well as the pathologic subtypes listed in Tables 3-5 herein. B-cell lymphomas are typically divided into low and high grade, typically corresponding to indolent (slow-growing) lymphomas and aggressive lymphomas, respectively. The present invention includes methods to treat both indolent and aggressive lymphomas.

According to certain embodiments, the present invention includes methods for treating, or delaying or inhibiting the growth of a tumor. In certain embodiments, the present invention includes methods to promote tumor regression. In certain embodiments, the present invention includes methods to reduce tumor cell load or to reduce tumor burden. In certain embodiments, the present invention includes methods to prevent tumor recurrence. The methods, according to this aspect of the invention, comprise sequentially administering a therapeutically effective amount of an anti-PD-1 antibody in combination with a bispecific anti-CD20/anti-CD3 antibody to a subject in need thereof, wherein each antibody is administered to the subject in multiple doses, e.g., as part of a specific therapeutic dosing regimen. For example, the therapeutic dosing regimen may comprise administering one or more doses of an anti-PD-1 antibody to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the one or more doses of anti-PD-1 antibody are administered in combination with one or more doses of a therapeutically effective amount of a bispecific anti-CD20/anti-CD3 antibody, wherein the one or more doses of the bispecific antibody are administered to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, each dose of the anti-CD20/anti-CD3 antibody is administered in more than 1 fractions, e.g., in 2-5 fractions ("split dosing") within the given dosing period. The anti-CD20/anti-CD3 bispecific antibody may be administered in split doses to reduce or eliminate the cytokine "spikes" induced in response to administration of the antibody. Cytokine spikes refer to the clinical symptoms of the cytokine release syndrome ("cytokine storm") and infusion related reactions, seen in patients administered anti-CD20 antibodies. In certain embodiments, the methods of the present invention comprise administering one or more doses of anti-PD-1 antibody in combination with one or more doses of a bispecific anti-CD20/anti-CD3 antibody to a subject in need thereof, wherein a dose of the bispecific antibody is administered as split doses, or in more than 1 fractions, e.g., as 2 fractions, as 3 fractions, as 4 fractions or as 5 fractions within the given dosing period. In certain embodiments, a dose of the bispecific antibody is split into 2 or more fractions, wherein each fraction comprises an amount of the antibody equal to the other fractions. For example, a dose of anti-CD20/anti-CD3 antibody comprising 1000 micrograms may be administered once a week, wherein the dose is administered in 2 fractions within the week, each fraction comprising 500 micrograms. In certain embodiments, a dose of the bispecific antibody is administered split into 2 or more fractions, wherein the fractions comprise unequal amounts of the antibody, e.g., more than or less than the first fraction. For example, a dose of anti-CD20/anti-CD3 antibody comprising 1000 micrograms may be administered once a week, wherein the dose is administered in 2 fractions within the week, wherein the first fraction comprises 700 micrograms and the second fraction comprises 300 micrograms. As another example, a dose of anti-CD20/anti-CD3 antibody comprising 1000 micrograms may be administered once in 2 weeks, wherein the dose is administered in 3 fractions within the 2-week period, wherein the first fraction comprises 400 micrograms, the second fraction comprises 300 micrograms and the third fraction comprises 300 micrograms.

In certain embodiments, the present invention includes methods to inhibit, retard or stop tumor metastasis or tumor infiltration into peripheral organs. The methods, according to this aspect, comprise administering a therapeutically effective amount of an anti-PD-1 antibody to a subject in need thereof. In certain embodiments, the anti-PD-1 antibody is administered in combination with a bispecific anti-CD20/anti-CD3 antibody.

In specific embodiments, the present invention provides methods for increased anti-tumor efficacy or increased tumor inhibition. The methods, according to this aspect of the invention, comprise administering to a subject with a B-cell cancer a therapeutically effective amount of an anti-PD-1 antibody prior to administering a therapeutically effective amount of a bispecific anti-CD20/anti-CD3 antibody, wherein the anti-PD-1 antibody may be administered about 1 day, more than 1 day, more than 2 days, more than 3 days, more than 4 days, more than 5 days, more than 6 days, more than 7 days, or more than 8 days prior to the bispecific antibody. In certain embodiments, the methods provide for increased tumor inhibition, e.g., by about 20%, more than 20%, more than 30%, more than 40% more than 50%, more than 60%, more than 70% or more than 80% as compared to a subject administered with the bispecific antibody prior to the anti-PD-1 antibody.

In certain embodiments, the methods of the present invention comprise administering a therapeutically effective amount of an anti-PD-1 antibody to a subject with a B-cell cancer. In specific embodiments, the B-cell cancer is Hodgkin's lymphoma or non-Hodgkin's lymphoma. In further embodiments, the B-cell cancer is indolent or aggressive. In certain embodiments, the subject is not responsive to prior therapy or has relapsed after prior therapy. In certain embodiments, the methods of the present invention further comprise administering a bispecific anti-CD20/anti-CD3 antibody to a subject with a CD20+B-cell cancer.

In certain embodiments, the methods of the present invention comprise administering a therapeutically effective amount of a bispecific anti-CD20/anti-CD3 antibody to a subject with a CD20+B-cell cancer. In specific embodiments, the B-cell cancer is acute lymphoblastic leukemia, or chronic lymphocytic leukemia. In further embodiments, the B-cell cancer is indolent or aggressive. In certain embodiments, the subject is not responsive to prior therapy or has relapsed after prior therapy (e.g., with an anti-CD20 inhibitor such as rituximab). In certain embodiments, the methods of the present invention further comprise administering an anti-PD-1 antibody to a subject with B-cell cancer.

In certain embodiments, the methods of the present invention comprise administering an anti-PD-1 antibody in combination with a bispecific anti-CD20/anti-CD3 antibody to a subject in need thereof as a "first line" treatment (e.g., initial treatment). In other embodiments, an anti-PD-1 antibody in combination with a bispecific anti-CD20/anti-CD3 antibody is administered as a "second line" treatment (e.g., after prior therapy). For example, an anti-PD-1 antibody in combination with a bispecific anti-CD20/anti-CD3 antibody is administered as a "second line" treatment to a subject that has relapsed after prior therapy with, e.g., chemotherapy or rituximab.

In certain embodiments, the methods of the present invention are used to treat a patient with a MRD-positive disease. Minimum residual disease (MRD) refers to small numbers of cancer cells that remain in the patient during or after treatment, wherein the patient may or may not show symptoms or signs of the disease. Such residual cancer cells, if not eliminated, frequently lead to relapse of the disease. The present invention includes methods to inhibit and/or eliminate residual cancer cells in a patient upon MRD testing. MRD may be assayed according to methods known in the art (e.g., MRD flow cytometry). The methods, according to this aspect of the invention, comprise administering an anti-PD-1 antibody in combination with a bispecific anti-CD20/anti-CD3 antibody to a subject in need thereof.

The methods of the present invention, according to certain embodiments, comprise administering to a subject a therapeutically effective amount of each of an anti-PD-1 antibody and a bispecific anti-CD20/anti-CD3 antibody in combination with a third therapeutic agent. The third therapeutic agent may be an agent selected from the group consisting of, e.g., radiation, chemotherapy, surgery, a cancer vaccine, a PD-L1 inhibitor (e.g., an anti-PD-L1 antibody), a LAG3 inhibitor (e.g., an anti-LAG3 antibody), a CTLA-4 inhibitor, a TIM3 inhibitor, a BTLA inhibitor, a TIGIT inhibitor, a CD47 inhibitor, an indoleamine-2,3-dioxygenase (IDO) inhibitor, a vascular endothelial growth factor (VEGF) antagonist, an Ang2 inhibitor, a transforming growth factor beta (TGFβ) inhibitor, an epidermal growth factor receptor (EGFR) inhibitor, an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., Bacillus Calmette-Guerin), granulocyte-macrophage colony-stimulating factor, a cytotoxin, a chemotherapeutic agent, an IL-6R inhibitor, an IL-4R inhibitor, an IL-10 inhibitor, a cytokine such as IL-2, IL-7, IL-21, and IL-15, an anti-inflammatory drug such as corticosteroids, and non-steroidal anti-inflammatory drugs, and a dietary supplement such as anti-oxidants. In certain embodiments, the antibodies may be administered in combination with therapy including a chemotherapeutic agent, radiation and surgery. As used herein, the phrase 'in combination with" means that the antibodies are administered to the subject at the same time as, just before, or just after administration of the third therapeutic agent. In certain embodiments, the third therapeutic agent is administered as a co-formulation with the antibodies. In a related embodiment, the present invention includes methods comprising administering a therapeutically effective amount of an anti-PD-1 antibody in combination with a bispecific anti-CD20/anti-CD3 antibody to a subject who is on a background anti-cancer therapeutic regimen. The background anti-cancer therapeutic regimen may comprise a course of administration of, e.g., a chemotherapeutic agent, or radiation. The anti-PD-1 antibody in combination with a bispecific anti-CD20/anti-CD3 antibody may be added on top of the background anti-cancer therapeutic regimen. In some embodiments, the antibodies are added as part of a "background step-down" scheme, wherein the background anti-cancer therapy is gradually withdrawn from the subject over time (e.g., in a stepwise fashion) while the antibodies are administered to the subject at a constant dose, or at an increasing dose, or at a decreasing dose, over time.

In certain embodiments, the methods of the present invention comprise administering to a subject in need thereof a therapeutically effective amount of an anti-PD-1 antibody in combination with a therapeutically effective amount of a bispecific anti-CD20/anti-CD3 antibody, wherein administration of the antibodies leads to increased inhibition of tumor growth. In certain embodiments, tumor growth is inhibited by at least about 10%, about 20%, about 30%, about 40%, about 50%, about 60%, about 70% or about 80% as compared to an untreated subject or a subject administered with either antibody as monotherapy. In certain embodiments, the administration of an anti-PD-1 antibody and/or a bispecific anti-CD20/anti-CD3 antibody leads to increased tumor regression, tumor shrinkage and/or disappearance. In certain embodiments, the administration of an anti-PD-1 antibody and/or a bispecific anti-CD20/anti-CD3 antibody leads to delay in tumor growth and development, e.g., tumor growth may be delayed by about 3 days, more than 3 days, about 7 days, more than 7 days, more than 15 days, more than 1 month, more than 3 months, more than 6 months, more than 1 year, more than 2 years, or more than 3 years as compared to an untreated subject or a subject treated with either antibody as monotherapy. In certain embodiments, administration of an anti-PD-1 antibody in combination with a bispecific anti-CD20/anti-CD3 antibody prevents tumor recurrence and/or increases duration of survival of the subject, e.g., increases duration of survival by more than 15 days, more than 1 month, more than 3 months, more than 6 months, more than 12 months, more than 18 months, more than 24 months, more than 36 months, or more than 48 months than an untreated subject or a subject which is administered either antibody as monotherapy. In certain embodiments, administration of the antibodies in combination increases progression-free survival or overall survival. In certain embodiments, administration of an anti-PD-1 antibody in combination with a bispecific anti-CD20/anti-CD3 antibody increases response and duration of response in a subject, e.g., by more than 2%, more than 3%, more than 4%, more than 5%, more than 6%, more than 7%, more than 8%, more than 9%, more than 10%, more than 20%, more than 30%, more than 40% or more than 50% over an untreated subject or a subject which has received either antibody as monotherapy. In certain embodiments, administration of an anti-PD-1 antibody and/or a bispecific anti-CD20/anti-CD3 antibody to a subject with a B-cell cancer leads to complete disappearance of all evidence of tumor cells ("complete response"). In certain embodiments, administration of an anti-PD-1 antibody and/or a bispecific anti-CD20/anti-CD3 antibody to a subject with a B-cell cancer leads to at least 30% or more decrease in tumor cells or tumor size ("partial response"). In certain embodiments, administration of an anti-PD-1 antibody and/or a bispecific anti-CD20/anti-CD3 antibody to a subject with a B-cell cancer leads to complete or partial disappearance of tumor cells/lesions including new measurable lesions. Tumor reduction can be measured by any of the methods known in the art, e.g., X-rays, positron emission tomography (PET), computed tomography (CT), magnetic resonance imaging (MRI), cytology, histology, or molecular genetic analyses.

In certain embodiments, the combination of administered antibodies is safe and well-tolerated by a patient wherein there is no increase in an adverse side effect [e.g., increased cytokine release ("cytokine storm") or increased T-cell activation] as compared to a patient administered with the bispecific antibody as monotherapy.

Anti-PD-1 Antibodies and Antigen-Binding Fragments Thereof

According to certain exemplary embodiments of the present invention, the methods comprise administering a therapeutically effective amount of an anti-PD-1 antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (IV) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for PD-1 or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind PD-1. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PD-1, as used in the context of the present invention, includes antibodies that bind PD-1 or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PD-1 may, however, have cross-reactivity to other antigens, such as PD-1 molecules from other (non-human) species.

According to certain exemplary embodiments of the present invention, the anti-PD-1 antibody, or antigen-binding fragment thereof comprises a heavy chain variable region (HCVR), light chain variable region (LCVR), and/or complementarity determining regions (CDRs) comprising any of the amino acid sequences of the anti-PD-1 antibodies as set forth in US Patent Publication No. 20150203579. In certain exemplary embodiments, the anti-PD-1 antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-PD-1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-PD-1 antibody or antigen-binding fragment thereof comprises an HCVR comprising SEQ ID NO: 1 and an LCVR comprising SEQ ID NO: 2. In certain embodiments, the methods of the present invention comprise the use of an anti-PD-1 antibody, wherein the antibody comprises a heavy chain comprising the amino acid sequence of SEQ ID NO: 9. In some embodiments, the anti-PD-1 antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-PD-1 antibody known as REGN2810. According to certain exemplary embodiments, the methods of the present invention comprise the use of REGN2810, or a bioequivalent thereof. The term "bioequivalent", as used herein, refers to anti-PD-1 antibodies or PD-1-binding proteins or fragments thereof that are pharmaceutical equivalents or pharmaceutical alternatives whose rate and/or extent of absorption do not show a significant difference with that of REGN2810 when administered at the same molar dose under similar experimental conditions, either single dose or multiple dose. In the context of the invention, the term refers to antigen-binding proteins that bind to PD-1 which do not have clinically meaningful differences with REGN2810 in their safety, purity and/or potency.

Other anti-PD-1 antibodies that can be used in the context of the methods of the present invention include, e.g., the antibodies referred to and known in the art as nivolumab (U.S. Pat. No. 8,008,449), pembrolizumab (U.S. Pat. No. 8,354,509), MEDI0608 (U.S. Pat. No. 8,609,089), pidilizumab (U.S. Pat. No. 8,686,119), or any of the anti-PD-1 antibodies as set forth in U.S. Pat. Nos. 6,808,710, 7,488, 802, 8,168,757, 8,354,509, 8,779,105, or 8900587.

The anti-PD-1 antibodies used in the context of the methods of the present invention may have pH-dependent binding characteristics. For example, an anti-PD-1 antibody for use in the methods of the present invention may exhibit reduced binding to PD-1 at acidic pH as compared to neutral pH. Alternatively, an anti-PD-1 antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PD-1 at acidic pH as compared to neutral pH" is expressed in terms of a ratio of the $K_D$ value of the antibody binding to PD-1 at acidic pH to the $K_D$ value of the antibody binding to PD-1 at neutral pH (or vice versa). For example, an antibody or antigen-binding fragment thereof may be regarded as exhibiting "reduced binding to PD-1 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Bispecific Anti-CD20/Anti-CD3 Antibodies

According to certain exemplary embodiments of the present invention, the methods comprise administering a therapeutically effective amount of a bispecific antibody that specifically binds CD3 and CD20. Such antibodies may be referred to herein as, e.g., "anti-CD20/anti-CD3," or "anti-CD20×CD3" or "CD20×CD3" bispecific antibodies, or other similar terminology.

As used herein, the expression "bispecific antibody" refers to an immunoglobulin protein comprising at least a first antigen-binding domain and a second antigen-binding domain. In the context of the present invention, the first antigen-binding domain specifically binds a first antigen (e.g., CD20), and the second antigen-binding domain specifically binds a second, distinct antigen (e.g., CD3). Each antigen-binding domain of a bispecific antibody comprises a heavy chain variable domain (HCVR) and a light chain variable domain (LCVR), each comprising three CDRs. In the context of a bispecific antibody, the CDRs of the first antigen-binding domain may be designated with the prefix "A" and the CDRs of the second antigen-binding domain may be designated with the prefix "B". Thus, the CDRs of the first antigen-binding domain may be referred to herein as A-HCDR1, A-HCDR2, and A-HCDR3; and the CDRs of the second antigen-binding domain may be referred to herein as B-HCDR1, B-HCDR2, and B-HCDR3.

The first antigen-binding domain and the second antigen-binding domain are each connected to a separate multimerizing domain. As used herein, a "multimerizing domain" is any macromolecule, protein, polypeptide, peptide, or amino acid that has the ability to associate with a second multimerizing domain of the same or similar structure or constitution. In the context of the present invention, the multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antibodies of the present invention typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antibodies of the present invention, Fc domains may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications are disclosed in US Patent Publication No. 20150266966, incorporated herein in its entirety.

The present invention also includes bispecific antibodies comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in US Patent Publication No. 20140243504, which is herein incorporated in its entirety. Chimeric Fc domains having these general structural arrangements, and variants thereof, can have altered Fc receptor binding, which in turn affects Fc effector function.

According to certain exemplary embodiments of the present invention, the bispecific anti-CD20/anti-CD3 antibody, or antigen-binding fragment thereof comprises heavy chain variable regions (A-HCVR and B-HCVR), light chain variable region (LCVR), and/or complementarity determining regions (CDRs) comprising any of the amino acid sequences of the bispecific anti-CD20/anti-CD3 antibodies as set forth in US Patent Publication No. 20150266966. In certain exemplary embodiments, the bispecific anti-CD20/anti-CD3 antibody or antigen-binding fragment thereof that can be used in the context of the methods of the present invention comprises: (a) a first antigen-binding arm comprising the heavy chain complementarity determining regions (A-HCDR1, A-HCDR2 and A-HCDR3) of a heavy chain variable region (A-HCVR) comprising the amino acid sequence of SEQ ID NO: 11 and the light chain complementarity determining regions (LCDRs) of a light chain variable region (LCVR) comprising the amino acid sequence of SEQ ID NO: 12; and (b) a second antigen-binding arm comprising the heavy chain CDRs (B-HCDR1, B-HCDR2 and B-HCDR3) of a HCVR (B-HCVR) comprising the amino acid sequence of SEQ ID NO: 13 and the light chain CDRs of a LCVR comprising the amino acid sequence of SEQ ID NO: 12. According to certain embodiments, the A-HCDR1 comprises the amino acid sequence of SEQ ID NO: 14; the A-HCDR2 comprises the amino acid sequence of SEQ ID NO: 15; the A-HCDR3 comprises the amino acid sequence of SEQ ID NO: 16; the LCDR1 comprises the amino acid sequence of SEQ ID NO: 17; the LCDR2 comprises the amino acid sequence of SEQ ID NO: 18; the LCDR3 comprises the amino acid sequence of SEQ ID NO: 19; the B-HCDR1 comprises the amino acid sequence of SEQ ID NO: 20; the B-HCDR2 comprises the amino acid sequence of SEQ ID NO: 21; and the B-HCDR3 comprises the amino acid sequence of SEQ ID NO: 22. In yet other embodiments, the bispecific anti-CD20/anti-CD3 antibody or antigen-binding fragment thereof comprises: (a) a first antigen-binding arm comprising a HCVR (A-HCVR) comprising SEQ ID NO: 11 and a LCVR comprising SEQ ID NO: 12; and (b) a second antigen-binding arm comprising a HCVR (B-HCVR) comprising SEQ ID NO: 13 and a LCVR comprising SEQ ID NO: 12.

Other bispecific anti-CD20/anti-CD3 antibodies that can be used in the context of the methods of the present invention include, e.g., any of the antibodies as set forth in US Patent Publication Nos. 20140088295 and 20150166661.

Combination Therapies

The methods of the present invention, according to certain embodiments, comprise administering to the subject an anti-CD20/anti-CD3 bispecific antibody in combination with an anti-PD-1 antibody. In certain embodiments, the methods of the present invention comprise administering the antibodies for additive or synergistic activity to treat cancer, preferably a heme cancer, more preferably, a B-cell cancer (e.g., non-Hodgkin's lymphoma or acute lymphoblastic leukemia). As used herein, the expression "in combination with" means that the anti-CD20/anti-CD3 bispecific antibody is administered before, after, or concurrent with the anti-PD-1 antibody. The term "in combination with" also includes sequential or concomitant administration of anti-PD-1 antibody and a bispecific anti-CD20/anti-CD3 antibody. For example, when administered "before" the bispecific anti-CD20/anti-CD3 antibody, the anti-PD-1 antibody may be administered more than 150 hours, about 150 hours, about 100 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the bispecific anti-CD20/anti-CD3 antibody. When administered "after" the bispecific anti-CD20/anti-CD3 antibody, the anti-PD-1 antibody may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the bispecific anti-CD20/anti-CD3 antibody. Administration "concurrent" with the bispecific anti-CD20/anti-CD3 antibody means that the anti-PD-1 antibody is administered to the subject in a separate dosage form within less than 5 minutes (before, after, or at the same time) of administration of the bispecific anti-CD20/anti-CD3 antibody, or administered to the subject as a single combined dosage formulation comprising both the anti-PD-1 antibody and the bispecific anti-CD20/anti-CD3 antibody.

In certain embodiments, the methods of the present invention comprise administration of a third therapeutic agent wherein the third therapeutic agent is an anti-cancer drug. As used herein, "anti-cancer drug" means any agent useful to treat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In certain embodiments, the methods of the present invention comprise administration of a third therapeutic agent selected from the group consisting of radiation, surgery, a cancer vaccine, a PD-L1 inhibitor (e.g., an anti-PD-L1 antibody), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., Bacillus Calmette-Guerin, a cancer vaccine), an adjuvant to increase antigen presentation (e.g., granulocyte-macrophage colony-stimulating factor), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), chimeric antigen receptor T cells (e.g., CD19-targeted T cells), an anti-inflammatory drug (e.g., corticosteroids, and non-steroidal anti-inflammatory drugs), and a dietary supplement such as anti-oxidants.

In certain embodiments, the methods of the invention comprise administering an anti-PD-1 antibody and an anti-CD20/anti-CD3 bispecific antibody in combination with radiation therapy to generate long-term durable anti-tumor responses and/or enhance survival of patients with cancer. In some embodiments, the methods of the invention comprise administering radiation therapy prior to, concomitantly or after administering an anti-PD-1 antibody and a bispecific anti-CD20/anti-CD3 antibody to a cancer patient. For example, radiation therapy may be administered in one or more doses to tumor lesions after administration of one or more doses of the antibodies. In some embodiments, radiation therapy may be administered locally to a tumor lesion to enhance the local immunogenicity of a patient's tumor (adjuvinating radiation) and/or to kill tumor cells (ablative radiation) after systemic administration of an anti-PD-1 antibody and/or a bispecific anti-CD20/anti-CD3 antibody. In certain embodiments, the antibodies may be administered in combination with radiation therapy and a chemotherapeutic agent (e.g., temozolomide or cyclophosphamide) or a VEGF antagonist (e.g., aflibercept).

Pharmaceutical Compositions and Administration

The present invention includes methods which comprise administering an anti-PD-1 antibody in combination with a bispecific anti-CD20/anti-CD3 antibody to a subject wherein the antibodies are contained within separate or combined (single) pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Administration Regimens

The present invention includes methods comprising administering to a subject an anti-PD-1 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved.

In certain embodiments, the present invention includes methods comprising administering to a subject a bispecific anti-CD20/anti-CD3 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the methods involve the administration of an anti-PD-1 antibody in combination with a bispecific anti-CD20/anti-CD3 antibody at a dosing frequency of about four times a week, twice a week, once a week, once every two weeks, once every three weeks, once every four weeks, once every five weeks, once every six weeks, once every eight weeks, once every nine weeks, once every twelve weeks, or less frequently so long as a therapeutic response is achieved.

According to certain embodiments of the present invention, multiple doses of an anti-PD-1 antibody in combination with a bispecific anti-CD20/anti-CD3 antibody may be administered to a subject over a defined time course. The methods according to this aspect of the invention comprise sequentially administering to a subject one or more doses of an anti-PD-1 antibody in combination with one or more doses of a bispecific anti-CD20/anti-CD3 antibody. As used herein, "sequentially administering" means that each dose of the antibody is administered to the subject at a different point in time, e.g., on different days separated by a predetermined interval (e.g., hours, days, weeks or months). The present invention includes methods which comprise sequentially administering to the patient a single initial dose of an anti-PD-1 antibody, followed by one or more secondary doses of the anti-PD-1 antibody, and optionally followed by one or more tertiary doses of the anti-PD-1 antibody. In certain embodiments, the methods further comprise sequentially administering to the patient a single initial dose of a bispecific anti-CD20/anti-CD3 antibody, followed by one or more secondary doses of the bispecific antibody, and optionally followed by one or more tertiary doses of the bispecific antibody.

According to certain embodiments of the present invention, multiple doses of an anti-PD-1 antibody and a bispecific anti-CD20/anti-CD3 antibody may be administered to a subject over a defined time course. The methods according to this aspect of the invention comprise sequentially administering to a subject multiple doses of an anti-PD-1 antibody and a bispecific anti-CD20/anti-CD3 antibody. As used herein, "sequentially administering" means that each dose of the anti-PD-1 antibody in combination with the bispecific antibody is administered to the subject at a different point in time, e.g., on different days separated by a predetermined interval (e.g., hours, days, weeks or months).

The terms "initial dose," "secondary doses," and "tertiary doses," refer to the temporal sequence of administration. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antibody (anti-PD-1 antibody or bispecific antibody). In certain embodiments, however, the amount contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an anti-PD-1 antibody may be administered to a patient with a B-cell cancer at a loading dose of about 1-3 mg/kg followed by one or more maintenance doses of about 0.1 to about 20 mg/kg of the patient's body weight.

In one exemplary embodiment of the present invention, each secondary and/or tertiary dose is administered ½ to 14 (e.g., ½, 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of anti-PD-1 antibody (and/or bispecific anti-CD20/anti-CD3 antibody) which is administered to a patient prior to the administration of the very next dose in the sequence with no intervening doses.

The methods according to this aspect of the invention may comprise administering to a patient any number of secondary and/or tertiary doses of an anti-PD-1 antibody (and/or bispecific anti-CD20/anti-CD3 antibody). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, one or more doses of an anti-PD-1 antibody and/or a bispecific anti-CD20/anti-CD3 antibody are administered at the beginning of a treatment regimen as "induction doses" on a more frequent basis (twice a week, once a week or once in 2 weeks) followed by subsequent doses ("consolidation doses" or "maintenance doses") that are administered on a less frequent basis (e.g., once in 4-12 weeks).

The present invention includes methods comprising sequential administration of an anti-PD-1 antibody in combination with a bispecific anti-CD20/anti-CD3 antibody, to a patient to treat a B-cell cancer (e.g., non-Hodgkin's lymphoma, acute lymphoblastic leukemia). In some embodiments, the present methods comprise administering one or more doses of an anti-PD-1 antibody followed by one or more doses of a bispecific anti-CD20/anti-CD3 antibody. In certain embodiments, the present methods comprise administering a single dose of an anti-PD-1 antibody followed by one or more doses of a bispecific anti-CD20/anti-CD3 antibody. In some embodiments, one or more doses of about 0.1 mg/kg to about 20 mg/kg of an anti-PD-1 antibody may be administered followed by one or more doses of about 0.1 mg/kg to about 10 mg/kg of the bispecific antibody to inhibit tumor growth and/or to prevent tumor recurrence in a subject with a B-cell cancer. In some embodiments, the anti-PD-1 antibody is administered at one or more doses followed by one or more doses of the bispecific antibody resulting in increased anti-tumor efficacy (e.g., greater inhibition of tumor growth, increased prevention of tumor recurrence as compared to an untreated subject or a subject administered with either antibody as monotherapy). Alternative embodiments of the invention pertain to concomitant administration of anti-PD-1 antibody and the bispecific antibody which is administered at a separate dosage at a similar or different frequency relative to the anti-PD-1 antibody. In some embodiments, the bispecific antibody is administered before, after or concurrently with the anti-PD-1 antibody. In certain embodiments, the bispecific antibody is administered as a single dosage formulation with the anti-PD-1 antibody.

Dosage

The amount of anti-PD-1 antibody and/or bispecific anti-CD20/anti-CD3 antibody administered to a subject according to the methods of the present invention is, generally, a therapeutically effective amount. As used herein, the phrase "therapeutically effective amount" means an amount of antibody (anti-PD-1 antibody or bispecific anti-CD20/anti-CD3 antibody) that results in one or more of: (a) a reduction in the severity or duration of a symptom of a B-cell cancer; (b) inhibition of tumor growth, or an increase in tumor necrosis, tumor shrinkage and/or tumor disappearance; (c) delay in tumor growth and development; (d) inhibit or retard or stop tumor metastasis; (e) prevention of recurrence of tumor growth; (f) increase in survival of a subject with a B-cell cancer; and/or (g) a reduction in the use or need for conventional anti-cancer therapy (e.g., reduced or eliminated use of chemotherapeutic or cytotoxic agents) as compared to an untreated subject or a subject administered with either antibody as monotherapy.

In the case of an anti-PD-1 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PD-1 antibody. In certain embodiments, 250 mg of an anti-PD-1 antibody is administered.

In the case of a bispecific anti-CD20/anti-CD3 antibody, a therapeutically effective amount can be from about 10 micrograms (mcg) to about 8000 mcg, e.g., about 10 mcg, about 20 mcg, about 50 mcg, about 70 mcg, about 100 mcg, about 120 mcg, about 150 mcg, about 200 mcg, about 250 mcg, about 300 mcg, about 350 mcg, about 400 mcg, about 450 mcg, about 500 mcg, about 550 mcg, about 600 mcg, about 700 mcg, about 800 mcg, about 900 mcg, about 1000 mcg, about 1050 mcg, about 1100 mcg, about 1500 mcg, about 1700 mcg, about 2000 mcg, about 2050 mcg, about 2100 mcg, about 2200 mcg, about 2500 mcg, about 2700 mcg, about 2800 mcg, about 2900 mcg, about 3000 mcg, about 4000 mcg, about 5000 mcg, about 6000 mcg, about 7000 mcg, or about 8000 mcg of the bispecific anti-CD20/anti-CD3 antibody.

The amount of either anti-PD-1 antibody or bispecific anti-CD20/anti-CD3 antibody contained within the individual doses may be expressed in terms of milligrams of antibody per kilogram of subject body weight (i.e., mg/kg). In certain embodiments, either anti-PD-1 antibody or bispecific anti-CD20/anti-CD3 antibody used in the methods of the present invention may be administered to a subject at a dose of about 0.0001 to about 100 mg/kg of subject body weight. For example, anti-PD-1 antibody may be administered at dose of about 0.1 mg/kg to about 20 mg/kg of a patient's body weight. The bispecific anti-CD20/anti-CD3 antibody may be administered at a dose of about 0.1 mg/kg to about 10 mg/kg of a patient's body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: In Vivo Efficacy of Anti-PD-1 Antibody in Combination with Anti-CD20×CD3 Bispecific Antibody Against B16_CD20 Tumors In this Example, the effect of PD-1 blockade in combination with CD20-targeted immunotherapy was examined against established B16_CD20 tumors in mice humanized for CD20 and CD3 using anti-mouse PD-1 and anti-human CD20×CD3 bispecific antibodies.

The exemplary bispecific anti-CD20/anti-CD3 antibody used in the Examples herein is "bsAb1" (also known as "Antibody 1" as disclosed in US20150266966), a fully human bispecific monoclonal antibody against CD20 and CD3 wherein the antibody comprises an anti-CD20 binding arm comprising a first heavy chain variable region (A-HCVR) comprising the amino acid sequence of SEQ ID NO: 11 and a light chain variable region (LCVR) comprising the amino acid sequence of SEQ ID NO: 12; and an anti-CD3 binding arm comprising a second heavy chain variable region (B-HCVR) comprising the amino acid sequence of SEQ ID NO: 13 and a LCVR comprising the amino acid sequence of SEQ ID NO: 12. The bispecific antibody bsAb1 comprises heavy and light chain CDR sequences comprising SEQ ID NOs: 14-22.

Mice humanized for CD20 and for CD3 were engineered using VelociGene® technology (Valenzuela et al 2003, Nat. Biotechnol. 21: 652-659), which were then interbred to generate double humanized CD20 CD3 mice (U.S. patent application Ser. No. 14/949,834, filed on Nov. 23, 2015).

Mice were subcutaneously implanted with $2.5 \times 10^5$ B16_CD20 cells on day −7. On day 0, thirty-five mice with tumor volumes between 25 and 115 mm$^3$ were selected and randomized into five treatment groups. Mice were treated twice a week with antibodies as follows: Group 1: control (PBS); Group 2: Isotype controls (a bivalent human antibody against an irrelevant antigen and a rat IgG2a control-BE0089 from BioXCell); Group 3: anti-hCD20×CD3 (bsAb1) (4 mg/kg); Group 4: anti-mouse PD-1 antibody (10 mg/kg; RMPI-14_rIgG2a; BioXCell); and Group 5: anti-hCD20×CD3 (bsAb1) (4 mg/kg)+anti-mouse PD-1 antibody (10 mg/kg). All antibodies were intraperitoneally administered. In Group 5, mice were concurrently treated with the antibodies. Tumor volumes were monitored by caliper measurement twice a week for the duration of the experiment and tumor-free animals were monitored for the absence of tumor recurrence for up to 80 days.

Anti-PD-1 and anti-CD20×CD3 monotherapy delayed tumor growth in mice with mice taking an average of 19 days to reach 500 mm³ of tumor volume. In contrast, mice treated with anti-PD-1 antibody in combination with anti-CD20×CD3 bispecific antibody took an average of 27 days to reach a tumor volume of 500 mm³ (FIG. 1 and Table 1).

TABLE 1

Tumor growth upon administration of anti-PD-1 antibody and bispecific anti-CD20/anti-CD3 antibody

| Treatment | Avg. days to reach 500 mm³ | Tumor free mice at day 30 |
|---|---|---|
| PBS | 15 | 0/7 |
| Isotype Controls | 15 | 0/7 |
| bsAb1 | 19 | 1/7 |
| Anti-PD-1 (rIgG2a) | 19 | 1/7 |
| bsAb1 + antiPD-1 | 27 | 4/7 |

Single-agent and combination treatment did not induce any change in body weight and no macroscopic signs of toxicity were observed in any treatment group.

The above experiment was repeated twice and in both cases, the combination treatment resulted in significant delay and inhibition of tumor growth as compared to the controls or to monotherapy with either anti-PD-1 antibody or the bispecific anti-CD20/CD3 antibody.

Example 2: In Vivo Efficacy of Anti-PD-1 Antibody and Anti-CD20×CD3 Bispecific Antibody Using a Sequential Dosing Regimen In this Example, the anti-tumor effect of anti-mouse PD-1 antibody in combination with anti-human CD20×CD3 bispecific antibody was examined using a sequential dosing regimen.

Double humanized CD20 CD3 mice were engineered using VelociGene® technology (Valenzuela et al 2003, Nat. Biotechnol. 21: 652-659; U.S. patent application Ser. No. 14/949,834, filed on Nov. 23, 2015).

Figure 2:
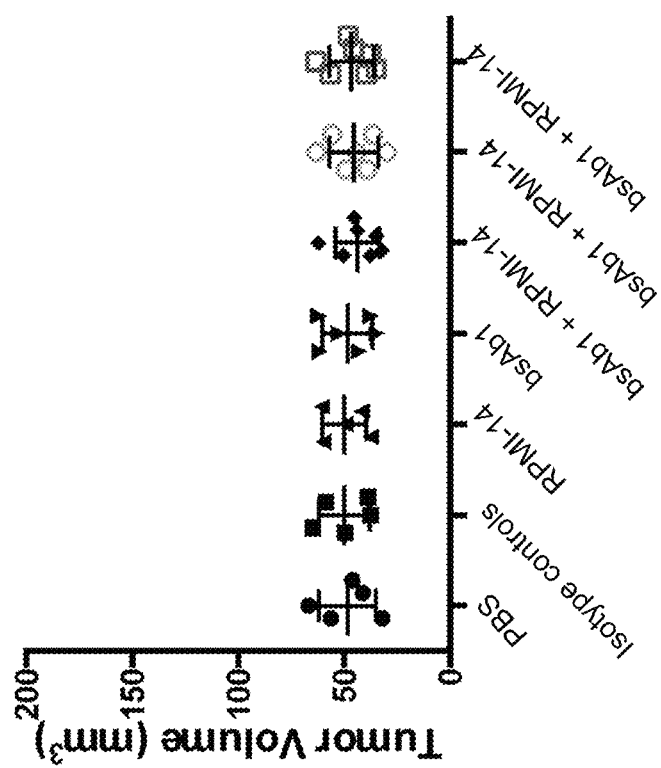
FIG. 2 shows mice randomized into cohorts based on tumor size (as described in Example 2 herein).

Mice were subcutaneously implanted with $2.5 \times 10^5$ B16_CD20 cells on day −7. On day 0, thirty-five mice with tumor volumes between 30 and 65 mm³ were selected and randomized into seven treatment groups (FIG. 2). Tumor growth was measured by calipers and body weights recorded twice a week for the entire length of the study. Mice were treated twice a week intraperitoneally with antibodies as follows: Group 1: control (PBS); Group 2: Isotype controls (a bivalent human antibody against an irrelevant antigen and a rat IgG2a control—BE0089 from BioXCell); Group 3: anti-mouse PD-1 antibody (10 mg/kg; RMPI-14_rIgG2a; BioXCell); Group 4: anti-hCD20×CD3 (bsAb1) (4 mg/kg); Group 5: anti-hCD20×CD3 (bsAb1) (4 mg/kg)+anti-mouse PD-1 antibody (10 mg/kg) dosed concurrently; Group 6: anti-mouse PD-1 antibody (10 mg/kg) followed by anti-hCD20×CD3 (bsAb1) (4 mg/kg); and Group 7: anti-hCD20×CD3 (bsAb1) (4 mg/kg) followed by anti-mouse PD-1 antibody (10 mg/kg). All antibodies were peritoneally administered using a sequential dosing regimen as shown in Table 2.

TABLE 2

Sequential dosing regimen

| | Gr. | Component #1 | Dosing Schedule - Component #1 | Component #2 | Dosing Schedule - Component #2 | # Mice |
|---|---|---|---|---|---|---|
| Controls | 1 | Vehicle | Starting Day 0 2x/week | Vehicle | Starting Day 0 2x/week | 5 |
| | 2 | Isotype Control | Starting Day 0 2x/week | Isotype Control | Starting Day 0 2x/week | 5 |
| | 3 | RMPI-14 (anti-PD-1) | Starting Day 0 2x/week | N/A | N/A | 5 |
| | 4 | N/A | N/A | bsAb1 | Starting Day 0 2x/week | 6 |
| Same-Time Dosing | 5 | RMPI-14 (anti-PD-1) | Starting Day 0 2x/week | bsAb1 | Starting Day 0 2x/week | 7 |
| Anti-PD-1 Then bsAb1 | 6 | RMPI-14 (anti-PD-1) | Starting Day 0 2x/week | bsAb1 | Starting Day 7 2x/week | 7 |
| bsAb1 Then anti-PD-1 | 7 | RMPI-14 (anti-PD-1) | Starting Day 7 2x/week | bsAb1 | Starting Day 0 2x/week | 7 |

Figure 3:
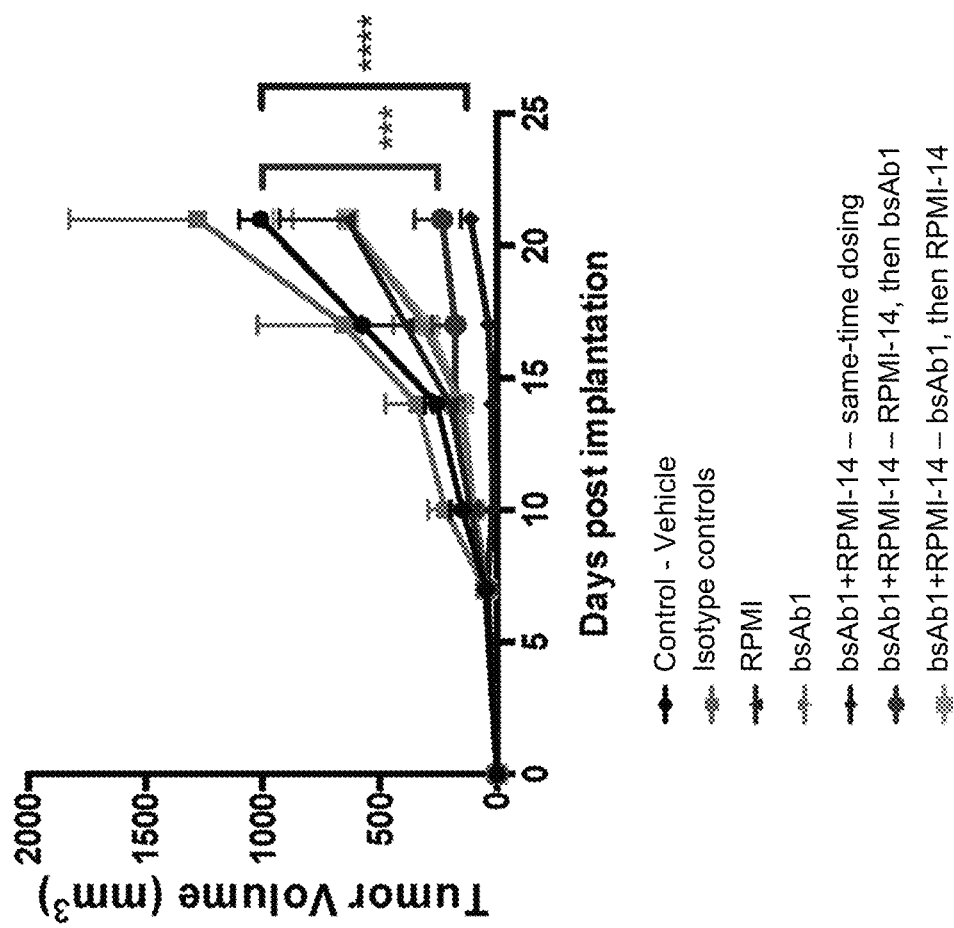
FIG. 3 summarizes the results of in vivo efficacy of anti-mouse PD-1 antibody alone and in combination with bispecific anti-CD20/anti-CD3 antibody against established B16_CD20+ tumors (described in Example 2 herein).

Dosing bsAb1 and anti-mouse PD-1 antibody at the same time or dosing anti-mPD-1 antibody followed by bsAb1 both demonstrated significant delay in tumor growth as compared to single-arm controls (FIG. 3). In the combination treatment where bsAb1 was given from D0 and anti-PD-1 antibody is given from D7, there was no delay in tumor growth compared to the single treatment arms of the study. No difference in weight loss or non-tumor-related lethality was observed upon the administration of the combination.

Example 3: Clinical Trial of Anti-PD-1 Antibody and Anti-CD20×CD3 Antibody in Patients with B-Cell Malignancies This study is an open-label, multicenter, dose escalation study with multiple dose escalation and expansion arms to investigate the efficacy, safety, and tolerability of anti-PD-1 antibody and anti-CD20/anti-CD3 bispecific antibody, alone and in combination, in adult patients with B-cell malignancies (including B-cell non-Hodgkin lymphoma, Hodgkin's lymphoma, and acute lymphoblastic leukemia).

The exemplary anti-PD-1 antibody used in this Example is REGN2810 (also known as H4H7798N as disclosed in US20150203579), a fully human monoclonal anti-PD-1 antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

The exemplary bispecific anti-CD20/anti-CD3 antibody used in this Example is bsAb1 (described in Example 1 herein).

The primary objective of the study is to assess safety, tolerability and dose-limiting toxicity (DLT) of: (i) single-agent REGN2810 in patients with lymphoma (B-cell non-Hodgkin lymphoma [B-NHL] and Hodgkin's lymphoma [HL]); (ii) single-agent bsAb1 in patients with Acute Lymphoblastic Leukemia (ALL); (iii) combination of bsAb1 and REGN2810 in patients with B-NHL; and (iv) combination of bsAb1 and REGN2810 in patients with ALL.

The secondary objectives of the study are: (i) to determine a recommended dose for: REGN2810 as a single-agent in patients with lymphoma (B-NHL and HL); bsAb1 as a single-agent in patients with ALL; bsAb1 and REGN2810 administered in combination in patients with B-NHL; and bsAb1 and REGN2810 administered in combination in patients with ALL; (ii) to characterize the pharmacokinetic (PK) profile of bsAb1 and REGN2810 when administered as single agents and in combination; (iii) to assess the immunogenicity of bsAb1 and REGN2810 when administered as single agents and in combination; and (iv) to study the preliminary antitumor activity of bsAb1 and REGN2810 when administered as single agents in specific indications and in combination, as measured by overall response rate, minimal residual disease (MRD) in patients with bone marrow disease at baseline, duration of response, progression-free survival, median, and rate at 6 and 12 months.

Additional objectives are to evaluate biomarkers that may correlate with mechanism of action, observed toxicity, and potential antitumor activity including, but not limited to: cytokine profiling; peripheral blood B- and T-cell subsets and immune phenotyping; changes in gene expression in peripheral blood; and serum immunoglobulin.

Study Population

The target population includes patients with lymphoma (B-NHL and HL) and ALL for whom no standard of care options exist. The various pathologic subtypes eligible for the different arms of the trial are listed in Tables 3-5.

TABLE 3

Pathologic subtype eligibility for treatment arms for lymphoma based on WHO classification: Single Agent REGN2810 Dose Escalation in B-NHL and HL Cohorts

| | |
|---|---|
| Hodgkin's Lymphoma (HL) | Nodular Sclerosis Classical HL<br>Lymphocyte-Rich Classical HL<br>Mixed Cellularity Classical HL<br>Lymphocyte-Depleted Classical HL<br>Nodular Lymphocyte Predominant HL |
| Mature B cell Neoplasms | Follicular lymphoma (FL) any grade<br>Small Lymphocytic lymphoma (SLL)<br>Lymphoplasmacytoid lymphoma (LPL)<br>Marginal zone lymphoma (MZL) (splenic, nodal, or extranodal)<br>Mantle Cell lymphoma (MCL)<br>Diffuse large B-cell Lymphoma (DLBCL), all subtypes<br>Diffuse large B-cell lymphoma (DLBCL), not otherwise specified<br>T cell/histiocyte rich large B-cell lymphoma<br>DLBCL associated with chronic inflammation<br>Epstein-Barr virus (EBV)+ DLBCL of the elderly<br>Lymphomatoid granulomatosis<br>Primary mediastinal (thymic) large B-cell lymphoma<br>Intravascular large B-cell lymphoma<br>Primary cutaneous DLBCL, leg type<br>B-cell lymphoma, unclassifiable, with features intermediate between DLBCL and Burkitt lymphoma<br>Burkitt Lymphoma |

TABLE 4

Pathologic subtype eligibility for treatment arms for lymphoma based on WHO classification: Single Agent REGN2810 Expansion Cohorts

| REGN2810 Single Agent Expansion in Hodgkin's Lymphoma | REGN2810 Single Agent Expansion in INDOLENT CD20+ B-NHL | REGN2810 Single Agent Expansion in AGGRESSIVE CD20+ B-NHL |
|---|---|---|
| Nodular Sclerosis Classical HL<br>Lymphocyte-Rich Classical HL<br>Mixed Cellularity Classical HL<br>Lymphocyte-Depleted Classical HL<br>Nodular Lymphocyte Predominant HL | MATURE B-CELL NEOPLASMS<br>FL (grade 1 or 2)<br>Lymphoplasmacytoid lymphoma (LPL)<br>MZL (splenic, nodal, or extranodal)<br>Small Lymphocytic lymphoma (SLL) | MATURE B-CELL NEOPLASMS<br>FL (grade 3)<br>Mantle Cell lymphoma (MCL)<br>DLBCL, all subtypes<br>DLBCL, not otherwise specified<br>T cell/histiocyte rich large B-cell lymphoma<br>DLBCL associated with chronic inflammation<br>Epstein-Barr virus (EBV)+ DLBCL of the elderly<br>Lymphomatoid granulomatosis<br>Primary mediastinal (thymic) large B-cell lymphoma<br>Intravascular large B-cell lymphoma<br>Primary cutaneous DLBCL, leg type<br>B-cell lymphoma, unclassifiable, with features intermediate between DLBCL and Burkitt lymphoma<br>Burkitt Lymphoma |

TABLE 5

Pathologic subtype eligibility for treatment arms for lymphoma based on WHO classification: bsAb1 and REGN2810 in Combination Dose Escalation and Expansion Cohorts

| Combination Dose Escalation in CD20+ B-NHL | Combination Expansion in INDOLENT CD20+ B-NHL | Combination Expansion in AGGRESSIVE CD20+ B-NHL |
|---|---|---|
| MATURE B-CELL NEOPLASMS | MATURE B-CELL NEOPLASMS | MATURE B-CELL NEOPLASMS |
| Follicular lymphoma (FL) any grade | FL (grade 1 or 2) | FL (grade 3) |
| Small Lymphocytic lymphoma (SLL) | Lymphoplasmacytoid lymphoma (LPL) | Mantle Cell lymphoma (MCL) |
| Lymphoplasmacytoid lymphoma (LPL) | MZL (splenic, nodal, or extranodal) | DLBCL, all subtypes |
| Marginal zone lymphoma (MZL) (splenic, nodal, or extranodal) | Small Lymphocytic lymphoma (SLL) | DLBCL, not otherwise specified |
| Mantle Cell lymphoma (MCL) | | T cell/histiocyte rich large B-cell lymphoma |
| Diffuse large B-cell Lymphoma (DLBCL), all subtypes | | DLBCL associated with chronic inflammation |
| Diffuse large B-cell lymphoma (DLBCL), not otherwise specified | | Epstein-Barr virus (EBV)+ DLBCL of the elderly |
| T cell/histiocyte rich large B-cell lymphoma | | Lymphomatoid granulomatosis |
| DLBCL associated with chronic inflammation | | Primary mediastinal (thymic) large B-cell lymphoma |
| Epstein-Barr virus (EBV)+ DLBCL of the elderly | | Intravascular large B-cell lymphoma |
| Lymphomatoid granulomatosis | | Primary cutaneous DLBCL, leg type |
| Primary mediastinal (thymic) large B-cell lymphoma | | B-cell lymphoma, unclassifiable, with features intermediate between DLBCL and Burkitt lymphoma |
| Intravascular large B-cell lymphoma | | Burkitt Lymphoma |
| Primary cutaneous DLBCL, leg type | | |
| B-cell lymphoma, unclassifiable, with features intermediate between DLBCL and Burkitt lymphoma | | |
| Burkitt Lymphoma | | |

Inclusion Criteria for B-NHL and HL Treatment Arms

A patient must meet the following criteria to be eligible for inclusion in the study: (1) Hematologic malignancy defined by either: a. NHL: Documented CD20+B-cell malignancy, with active disease that is either refractory to or relapsed after most recent prior therapy, for whom no standard of care options exist, and for whom treatment with an anti-CD20 antibody may be appropriate: i. B-NHL per WHO 2008 criteria (Campo 2011), b. Documented HL, per WHO 2008 criteria (Campo 2011), with active disease not responsive to prior therapy or relapsed after prior therapy for whom no standard of care options exist (REGN2810 single-agent therapy cohorts ONLY): (2) All patients must have at least 1 bi-dimensionally measurable lesion ($\geq 1.5$ cm) documented by diagnostic imaging (CT, PET-CT, or MRI); (3) Age $\geq 18$ years; (4) Eastern Cooperative Oncology Group (ECOG) performance status$\leq 1$; (5) Life expectancy of at least 6 months; (6) Adequate bone marrow function documented by: a. Platelet counts $\geq 75 \times 10^9$/L b. Hemoglobin level $\geq 9$ g/dL c. ANC $\geq 1 \times 10^9$/L (NOTE: Patients with cell counts below thresholds listed above may be considered for enrollment if, in the opinion of the investigator, the reason is believed to be due to current bone marrow infiltration by underlying malignancy. In such cases, the investigator must discuss the eligibility with the sponsor and receive approval for enrollment in writing.); (7) Adequate hepatic function: a. Total bilirubin$\leq 1.5 \times$upper limit of normal (ULN) ($\leq 3 \times$ULN if liver involvement) b. Transaminases$\leq 2.5 \times$ULN ($\leq 5 \times$ULN if liver involvement) c. Alkaline phosphatase$\leq 2.5 \times$ULN ($\leq 5 \times$ULN if liver involvement) (NOTE: Patients with liver involvement of their malignancy with concomitant $3 \times$ULN$\leq$ aspartate aminotransferase (AST) and/or alanine aminotransferase (ALT)$\leq 5 \times$ULN AND 1.5$\times$ULN$\leq$ total bilirubin$\leq 3 \times$ULN will be excluded. NOTE: Patients with Gilbert's syndrome do not need to meet this requirement provided their total bilirubin is unchanged from their baseline. NOTE: Patients may be considered for enrollment if, in the opinion of the investigator, the abnormal laboratory results are due to current underlying malignancy. In such cases, the investigator must discuss the eligibility with the sponsor and receive approval for enrollment in writing.); (8) Serum creatinine$\leq 1.5 \times$ULN or calculated creatinine clearance by Cockcroft-Gault $\geq 50$ mL/min (NOTE: Patients with creatinine clearance by Cockcroft-Gault that does not meet criteria may be considered for enrollment if a measured creatinine clearance (based on 24-hour urine or other reliable method) is $\geq 50$ mL/min. NOTE: Patients may be considered for enrollment if, in the opinion of the investigator, the abnormal laboratory results are due to current underlying malignancy. In such cases, the investigator must discuss the eligibility with the sponsor and receive approval for enrollment in writing.); (9) Normal cardiac ejection fraction by pretreatment MUGA or echocardiogram within 4 weeks prior to enrollment within the normal range of values for the institution; (10) Willingness to undergo mandatory tumor biopsy pretreatment, if in the opinion of the investigator, the patient has an accessible lesion that can be biopsied without significant risk to the patient: (11) Willing and able to comply with clinic visits and study-related procedures; and (12) Provide signed informed consent.

Exclusion Criteria for B-NHL and HL Treatment Arms

A patient who meets any of the following criteria will be excluded from the study: (1) Primary central nervous system (CNS) lymphoma, or known or suspected CNS involvement by nonprimary CNS NHL; (2) History of or current relevant CNS pathology such as: a. Epilepsy, seizure, paresis, aphasia, apoplexia, severe brain injuries, cerebellar disease, organic brain syndrome, psychosis, or b. Evidence for presence of inflammatory lesions and/or vasculitis on cerebral MRI during screening; (3) Ongoing or recent (within 2 years) evidence of significant autoimmune disease that required treatment with systemic immunosuppressive treatments, which may suggest risk for iAEs; (4) Standard anti-lymphoma chemotherapy (nonbiologic) or radiotherapy less than 28 days prior to first administration of study drug(s); (5) Treatment with an investigational nonbiologic agent less than 28 days prior to first administration of study drug(s); (6) Treatment with alemtuzumab less than 12 weeks of first administration of study drug(s); (7) Treatment with rituximab, immune-modulating agents or other investigational or commercial biologic agent less than 28 days prior to first administration of study drug(s). Examples of immune-modulating agents include blockers of CTLA-4, 4-1BB (CD137), LAG3, OX-40, therapeutic vaccines, or cytokine treatments; (8) Prior allogeneic stem cell transplantation; (9) Prior treatment with an agent that blocks the PD-1/PD-L1 pathway, unless the patient demonstrated benefit (applicable only for patients in single-agent REGN2810 therapy) (Note: Such patients should be discussed with the sponsor's medical monitor before enrollment); (10) Concurrent active malignancy for which the patient is receiving treatment; (11) Evidence of significant concurrent disease or medical condition that could interfere with the conduct of the study, or put the patient at significant risk including, but not limited to, significant cardiovascular disease (eg, New York Heart Association Class III or IV cardiac disease, myocardial infarction within 6 months prior to screening, unstable arrhythmias or unstable angina) and/or significant pulmonary disease (eg, obstructive pulmonary disease and history of symptomatic bronchospasm); (12) Known active bacterial, viral, fungal, mycobacterial or other infection or any major episode of infection requiring hospitalization or treatment with IV anti-infectives within 14 days prior to first administration of study drug; (13) Infection with human immunodeficiency virus (HIV) or active infection with hepatitis B virus (HBV) or hepatitis C virus (HCV); (14) History of pneumonitis within the last 5 years; (15) History of allergic reactions attributed to compounds of similar chemical or biologic composition of study drug(s); (16) History of hypersensitivity to any compound in the tetracycline antibiotics group (precaution due to potential presence of trace components in study drug material); (17) Known hypersensitivity to both allopurinol and rasburicase; (18) Pregnant or breastfeeding women; and (19) Sexually active men or women of childbearing potential who are unwilling to practice adequate contraception during the study and up to 6 months after discontinuation of study medication.

Inclusion Criteria for Acute Lymphoblastic Leukemia Study Arms

A patient must meet the following criteria to be eligible for inclusion in the study: (1) Documented relapsed or refractory CD20+(defined as CD20 expression by flow cytometry on ≥20% of leukemic lymphoblasts) B-lineage ALL after at least induction and 1 cycle of consolidation chemotherapy a. Patients with Philadelphia chromosome positive ALL are required to have failed or be intolerant to at least 1 tyrosine-kinase inhibitor NOTE: Patients with chronic myeloid leukemia (CML) blast crisis with lymphoid phenotype are allowed, provided they meet inclusion criterion #1; (2) Age ≥18 years; (3) ECOG performance status≤2; (4) CNS negative disease, confirmed by lumbar puncture, within 28 days of starting study drug (see Appendix A); (5) Adequate bone marrow function documented by: a. Platelet counts ≥10×10$^9$/L b. Hb level ≥7 g/dl c. Absolute phagocyte count ≥0.5×10$^9$/L (phagocytes: neutrophils, bands and monocytes); (6) Adequate hepatic function: a. Total bilirubin≤1.5×ULN (≤3×ULN if liver involvement) b. Transaminases≤2.5×ULN (≤5×ULN if liver involvement) c. Alkaline phosphatase≤2.5×ULN (≤5×ULN if liver involvement) (NOTE: Patients with Gilbert's syndrome do not need to meet this requirement provided their total bilirubin is unchanged from their baseline. NOTE: Patients may be considered for enrollment if, in the opinion of the investigator, the abnormal laboratory results are due to current underlying malignancy. In such cases, the investigator must discuss the eligibility with the sponsor and receive approval for enrollment in writing.); (7) Serum creatinine≤1.5×ULN or calculated creatinine clearance by Cockcroft-Gault ≥50 mL/min (NOTE: Patients with creatinine clearance by Cockcroft-Gault that does not meet criteria may be considered for enrollment if a measured creatinine clearance (based on 24-hour urine or other reliable method) is ≥50 mL/min. NOTE: Patients may be considered for enrollment if, in the opinion of the investigator, the abnormal laboratory results are due to current underlying malignancy. In such cases, the investigator must discuss the eligibility with the sponsor and receive approval for enrollment in writing.); (8) No sign of acute or chronic graft versus host disease (GvHD) and no anti-GvHD medication within 14 days prior to initiation of study drug(s); (9) Normal cardiac ejection fraction by pretreatment MUGA or echocardiogram within 4 weeks prior to enrollment within the normal range of values for the institution; (10) Willing and able to comply with clinic visits and study-related procedures; and (11) Provide signed informed consent.

Exclusion Criteria for Acute Lymphoblastic Leukemia Treatment Arms

A patient who meets any of the following criteria will be excluded from the study: (1) History of or current relevant CNS pathology such as a. Epilepsy, seizure, paresis, aphasia, apoplexia, severe brain injuries, cerebellar disease, organic brain syndrome, psychosis, or b. Evidence for presence of inflammatory lesions and/or vasculitis on cerebral MRI during screening; (2) Burkitt's leukemia; (3) Current testicular involvement of leukemia; (4) Ongoing or recent (within 2 years) evidence of significant autoimmune disease (with the exception of GvHD) that required treatment with systemic immunosuppressive treatments, which may suggest risk for iAEs; (5) Standard anti-leukemia chemotherapy (nonbiologic) or radiotherapy less than 14 days prior to first administration of study drug(s); (6) Treatment with an investigational nonbiologic agent less than 14 days prior to first administration of study drug(s); (7) Treatment with rituximab, immune modulating agents or other investigational or commercial biologic agent less than 14 days prior to first administration of study drug. (Examples of immune modulating agents include blockers of CTLA-4, 4-1BB (CD137), LAG3, OX-40, therapeutic vaccines, or cytokine treatments); (8) Treatment with alemtuzumab, less than 12 weeks prior to first administration of study drug(s); (9) Prior allogeneic stem cell transplantation within 3 months of treatment; (10) Concurrent active malignancy for which the patient is receiving treatment; (11) Evidence of significant concurrent disease or medical condition that could interfere with the conduct of the study, or put the patient at significant risk including, but not limited to, significant cardiovascular disease (eg, New York Heart Association Class III or IV cardiac disease, myocardial infarction within 6 months prior to screening, unstable arrhythmias or unstable angina) and/or significant pulmonary disease (eg, obstructive pulmonary disease and history of symptomatic bronchospasm); (12) Known active bacterial, viral, fungal, mycobacterial or other infection or any major episode of infection requiring hospitalization or treatment with IV anti-infectives within 14 days prior to first administration of study drug(s); (13) Infection with HIV or active infection with HBV or HCV; (14) History of pneumonitis within the last 5 years; (15) History of allergic reactions attributed to compounds of similar chemical or biologic composition of study drug(s); (16) History of hypersensitivity to any compound in the tetracycline antibiotics group (precaution due to potential presence of trace components in study drug material); (17) Known hypersensitivity to both allopurinol and rasburicase; (18) Pregnant or breastfeeding women; and (19) Sexually active men or women of childbearing potential who are unwilling to practice adequate contraception during the study and up to 6 months after discontinuation of study medication.

Study Design

This is an open-label, multicenter, dose escalation study with multiple dose escalation and expansion arms. Patients are assigned to one of the following arms: single-agent REGN2810, single-agent bsAb1, or a combination of both drugs, depending on the patient's diagnosis, and on the stage of the study at the time of enrollment.

Figure 4:
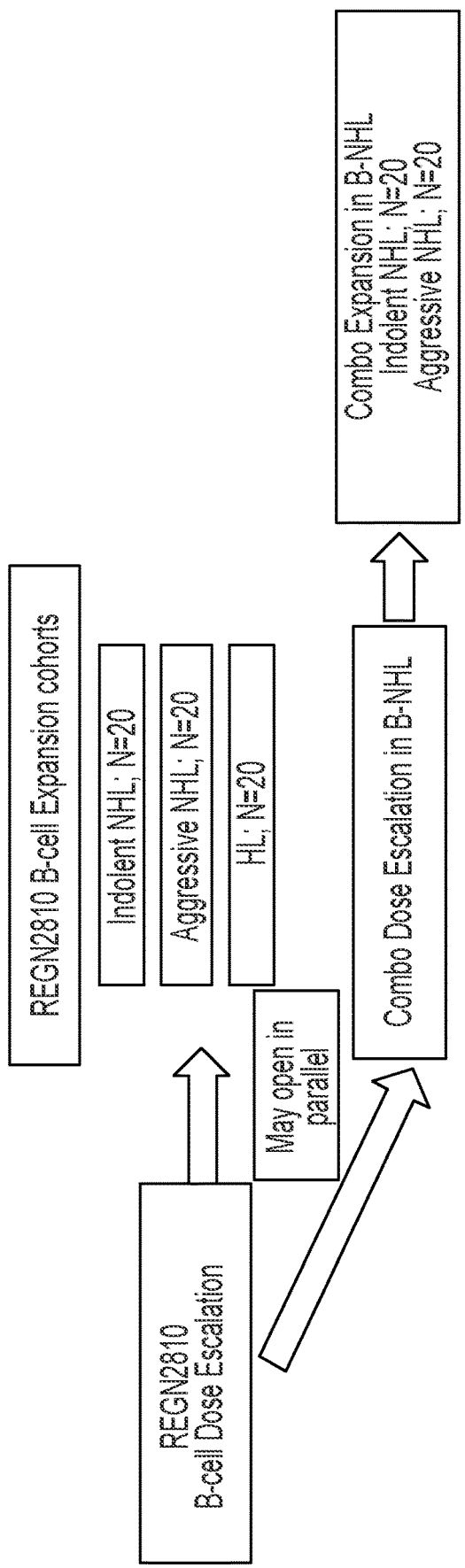
FIG. 4 shows a schematic representation of the treatment arms and dose cohorts for patients with lymphoma (B-cell non-Hodgkin's lymphoma and Hodgkin's lymphoma) (described in Example 3 herein).
Figure 5:
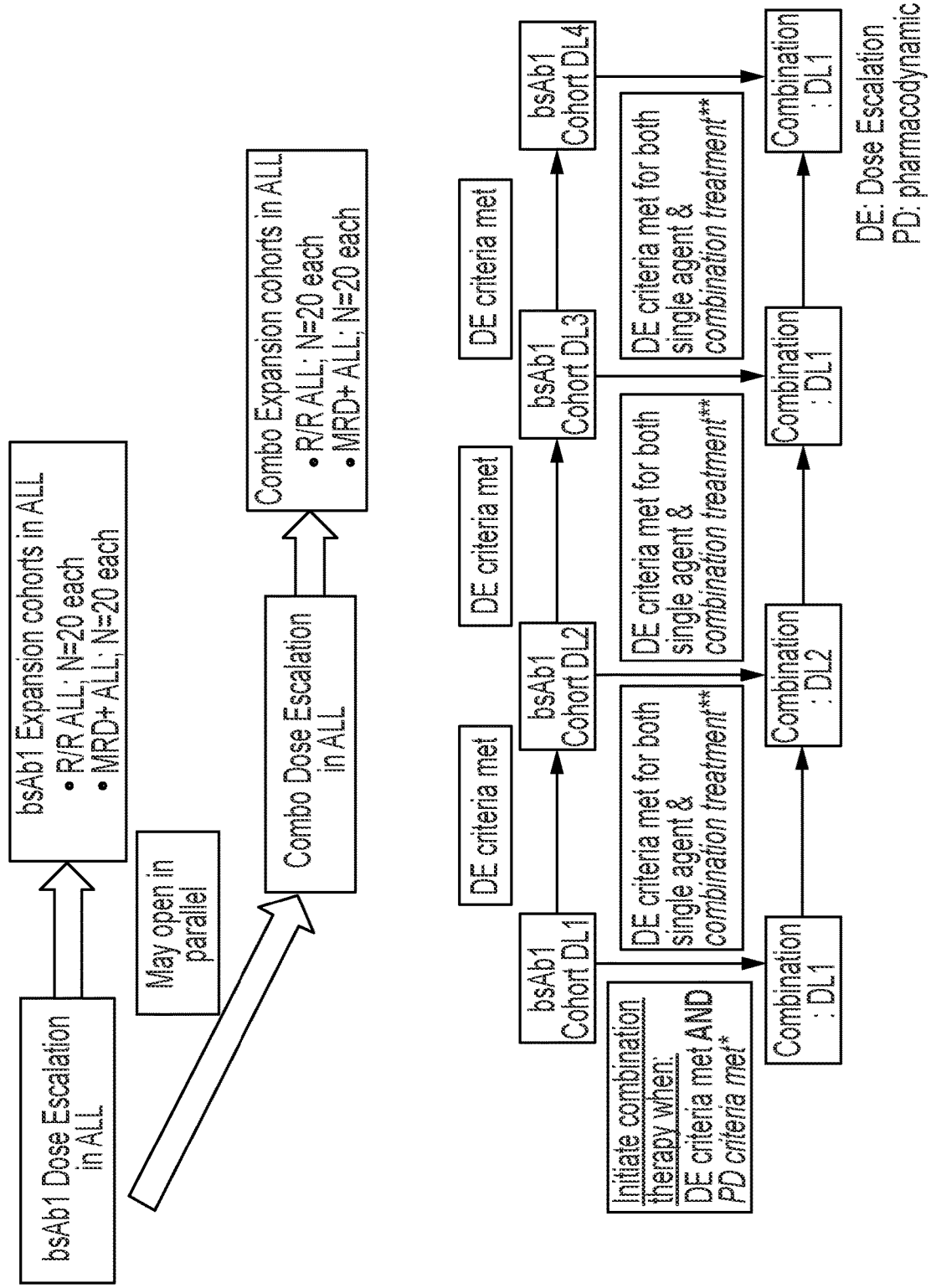
FIG. 5 shows a schematic representation of the treatment arms and dose cohorts for patients with acute lymphoblastic leukemia (described in Example 3 herein).

Treatment arms and dose cohorts for patients with lymphoma (B-NHL and HL) are detailed in FIG. 4. Patients are assigned to one of the following cohorts: Single-agent REGN2810 arms in patients with lymphoma (B-NHL and HL)
  2 dose escalation cohorts (1 mg/kg and 3 mg/kg)
  3 expansion cohorts: a) indolent B-NHL, b) aggressive B-NHL, and c) HL
Combination Treatment Arms in Patients with B-NHL
  Multiple dose escalation cohorts
  2 expansion cohorts: a) indolent B-NHL, and b) aggressive B-NHL Single-agent and combination treatment cohorts for patients with ALL are detailed in FIG. 5. Patients are assigned to one of the following cohorts: Single-agent bsAb1 arms in patients with ALL
  Multiple dose escalation cohorts
  2 expansion cohorts: a) relapsed/refractory ALL, and b) minimal residual disease-positive (MRD+) ALL
Combination Treatment Arms in Patients with ALL
  Multiple dose escalation cohorts
  2 expansion cohorts: a) relapsed/refractory ALL and b) MRD-positive ALL Treatment with combination therapy is initiated after single-agent data is submitted and reviewed by the relevant health authority.
Single-Agent REGN2810 in Patients with Lymphoma (B-NHL and HL)

Figure 6:
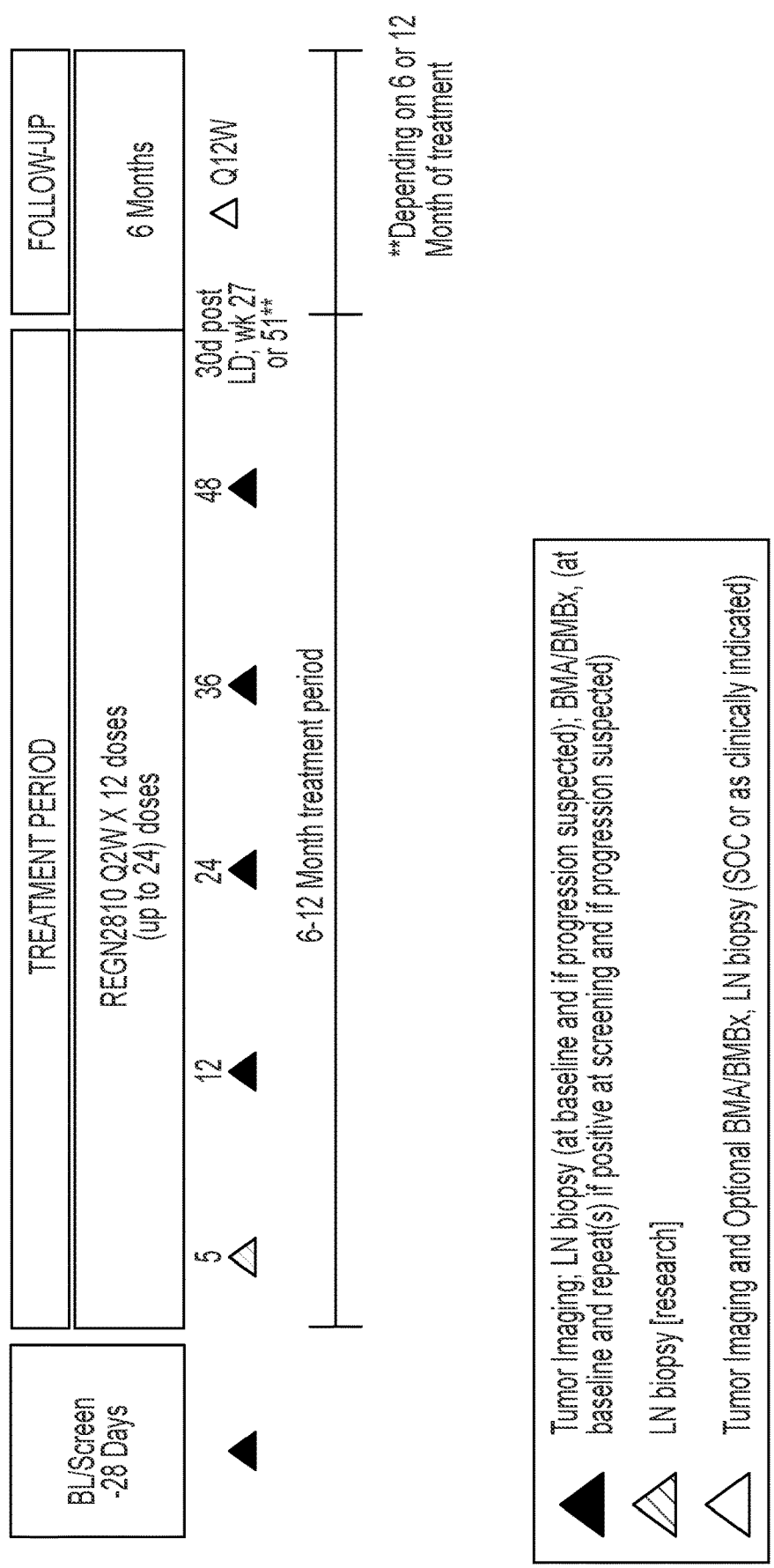
FIG. 6 is a study flow diagram of treatment schedule with single agent anti-PD-1 antibody (REGN2810) for patients with lymphoma (B-cell non-Hodgkin's lymphoma and Hodgkin's lymphoma) (described in Example 3 herein).
Figure 7:
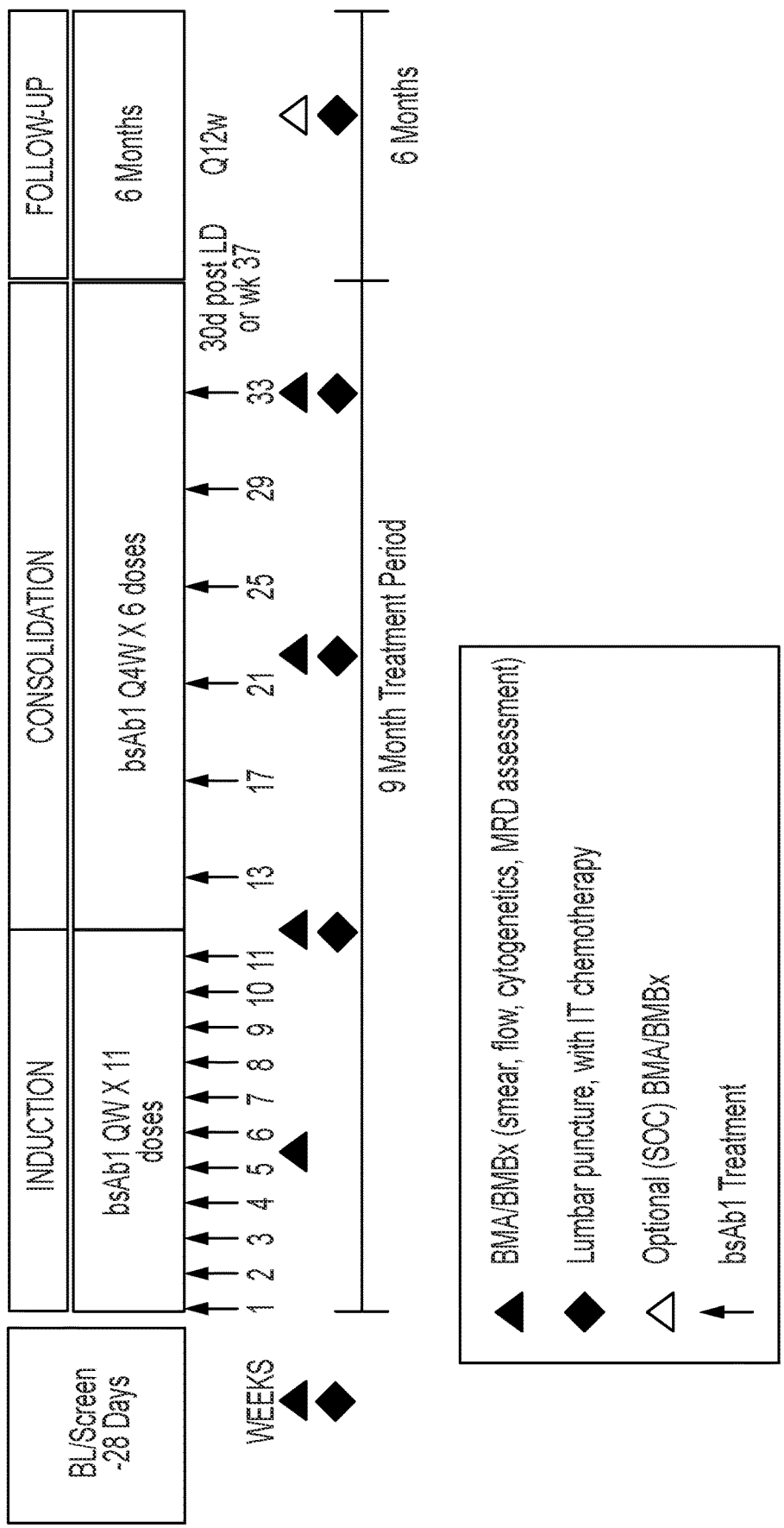
FIG. 7 is a study flow diagram of treatment schedule with single agent anti-CD20/anti-CD3 bispecific antibody (bsAb1) for patients with acute lymphoblastic leukemia (described in Example 3 herein).

FIG. 6 shows single-agent REGN2810 treatment schedule for patients with lymphoma. Patients are administered REGN2810 IV every 2 weeks (Q2W) at a specified dose level (DL). Patients receive REGN2810 for a minimum of 12 doses (24 weeks) and up to a maximum of 24 doses (48 weeks). After a minimum of 24 weeks of treatment and after consultation with the investigator and the sponsor, patients with tumor burden assessments of complete response, stable disease or partial response that have been unchanged for 3 successive tumor evaluations may also elect to discontinue treatment. Upon completion of treatment (24 or 48 weeks), there will be a 24-week (6 month) follow-up period.
Single-Agent bsAb1 in Patients with ALL FIG. 7 shows single-agent bsAb1 treatment schedule for patients with ALL. Patients are assigned a DL that will consist of an initial starting dose followed by a subsequent higher dose, provided the initial starting dose was tolerated (Table 6).

TABLE 6

Dose levels for bsAb1

| Dose Level | Initial dose (flat mcg) | Subsequent dose (flat mcg) |
| --- | --- | --- |
| DL-1 | 10 | 30 |
| DL1 | 30 | 100 |
| DL2 | 100 | 300 |
| DL3 | 300 | 1000 |
| DL4 | 1000 | 2000 |
| DL5 | 1000 | 3000 |
| DL6 | 1000 | 4000 |
| DL7 | 1000 | 5000 |

Figure 8:
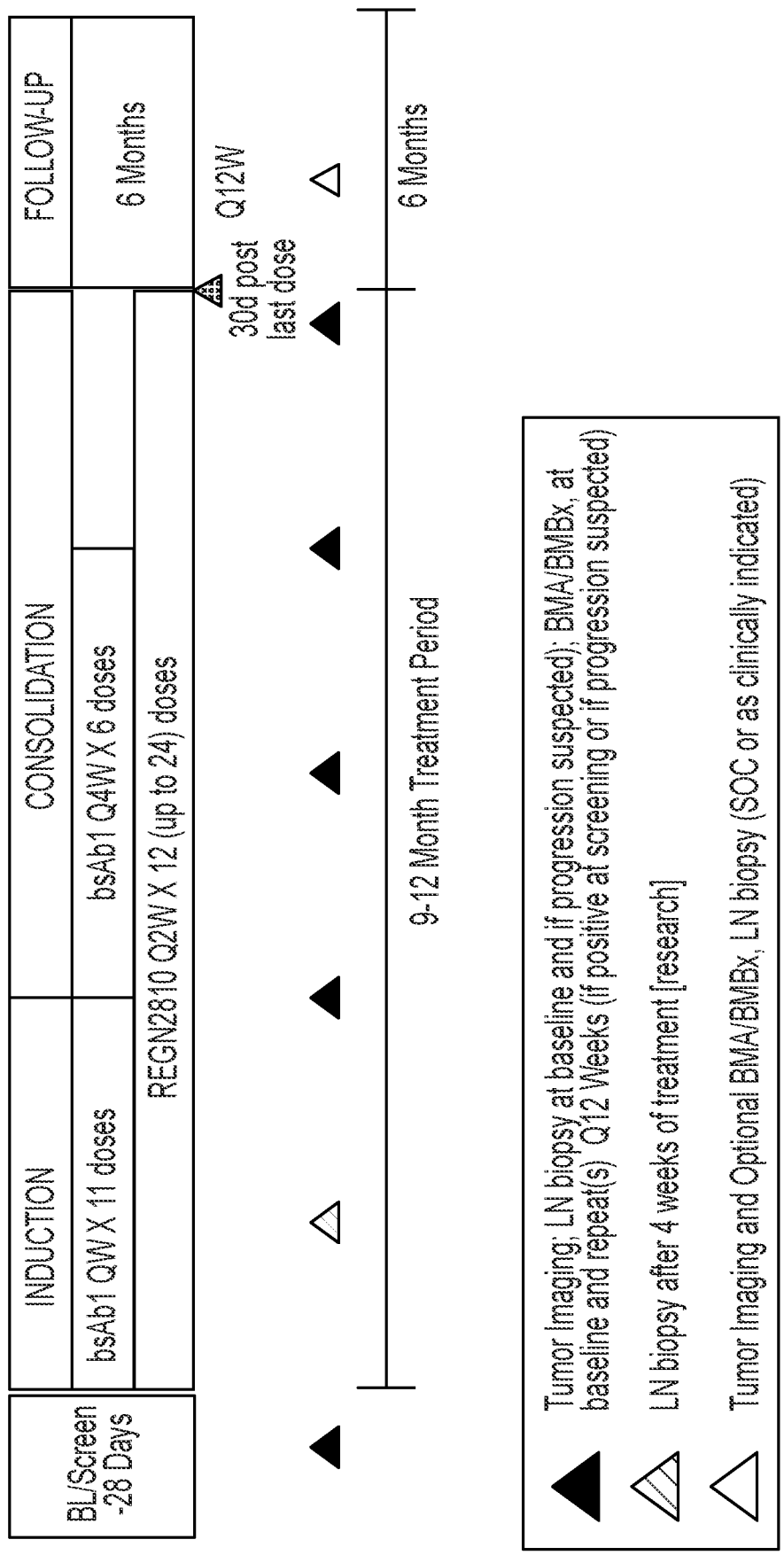
FIG. 8 is a study flow diagram of bsAb1+REGN2810 combination treatment schedule for patients with B-cell non-Hodgkin's lymphoma (described in Example 3 herein).
Figure 9:
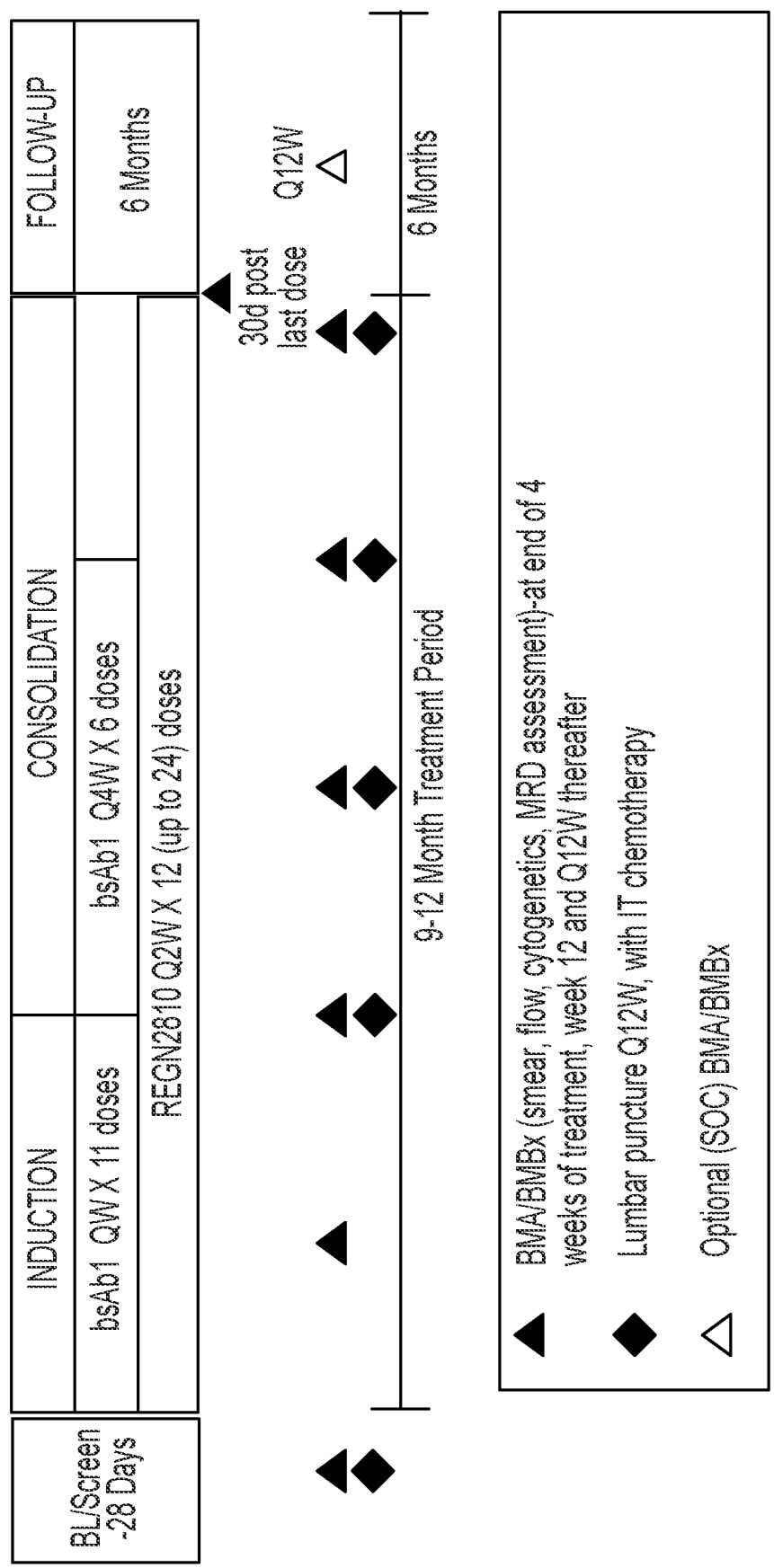
FIG. 9 is a study flow diagram of bsAb1+REGN2810 combination treatment schedule for patients with acute lymphoblastic leukemia (described in Example 3 herein).

Intravenous bsAb1 is administered weekly for 11 doses, followed by treatment every 4 weeks (Q4W) starting at week 13, for 6 additional doses. Patients are followed for an additional 6 months after completion of bsAb1 treatment.
Combination Therapy There are 2 separate combination arms; one for patients with B-NHL and another for patients with ALL. FIG. 8 shows the combination treatment schedule for patients with B-NHL and FIG. 9 shows the combination treatment schedule for patients with ALL.

Patients are administered REGN2810 IV Q2W at a specified DL (0.3, 1, or 3 mg/kg). Patients receive REGN2810 for a minimum of 12 doses (24 weeks) and up to a maximum of 24 doses (48 weeks). After a minimum of 24 weeks of treatment and after consultation with the investigator and the sponsor, patients with tumor burden assessments of complete response, stable disease or partial response that have been unchanged for 3 successive tumor evaluations may also elect to discontinue treatment.

Patients will be assigned a bsAb1 DL that will consist of an initial starting dose followed by a subsequent higher dose, provided the initial starting dose was tolerated (Table 6). Intravenous bsAb1 will be administered weekly for 11 doses, followed by treatment Q4W starting at week 13, for 6 additional doses.

On study visits in which both bsAb1 and REGN2810 are administered, REGN2810 will be administered first. Patients will be followed for at least an additional 6 months after completion of bsAb1 treatment. The start of follow-up will depend on how long the patient is treated with REGN2810 (24 or 48 weeks).
Starting Doses Single agent REGN2810: The starting dose for REGN2810 in patients with lymphoma is 1 mg/kg once in 2 weeks, in the absence of unexpected safety observations. Single-agent REGN2810 expansions in indolent B-NHL, aggressive B-NHL, and HL are determined in the single-agent REGN2810 dose escalation arm in patients with lymphoma (B-NHL and HL).

Single agent bsAb1: The starting DL of single-agent bsAb1 in patients with ALL is based on the safety observed. The starting dose of the initial DL in patients with ALL will be at least 10 times lower than the initial dose of the DL that has cleared safety; however, the starting DL will not be lower than DL1. Single-agent bsAb1 expansions in relapsed/refractory ALL and MRD-positive ALL is determined in the ALL dose escalation arm.

Combination arm—Patients with B-NHL: The dose of REGN2810 when administered in combination with bsAb1 in patients with B-NHL is planned to be 3 mg/kg Q2W, provided there are no unexpected safety observations in single-agent REGN2810 dose escalation in B-cell malignancies. The starting DL of bsAb1 when administered in combination with REGN2810 in patients with B-NHL will be 1 DL lower than that which has cleared safety and will not be lower than DL1.

Combination arm—Patients with ALL: The dose of REGN2810 when administered in combination with bsAb1 in patients with ALL is planned to be 3 mg/kg Q2W, provided there are no unexpected safety observations in single-agent REGN2810 dose escalation in B-cell malignancies. The starting DL of bsAb1 when administered in combination with REGN2810 in patients with ALL will be at a DL that has cleared safety and has demonstrated evidence of minimal biologic activity in the single-agent bsAb1 dose escalation arm in patients with ALL in the current study. Minimal biologic activity is defined as evidence of reduction of bone marrow blasts by 50% (partial response) at the bone marrow assessment performed at week 5 in at least 1 of 3 patients treated at the specified dose level.

Dose Escalation

In all arms and all cohorts, dose escalation rules will follow a traditional 3+3 dose escalation design, enrolling between 3 and 6 patients per cohort.

The dose limiting toxicity (DLT) observation period is defined as the first 28 days of treatment for all cohorts in all arms. Any of the following events occurring in the first 28 days of treatment (and considered to be related to study treatment by the investigator) is considered a DLT: grade ≥2 uveitis, grade 4 neutropenia, grade 4 thrombocytopenia, and grade ≥3 febrile neutropenia.

The maximum tolerated dose (MTD) is determined based on observed toxicity during the DLT observation period, and is defined as the dose level (DL) immediately below the level at which dosing is stopped due to the occurrence of DLTs in 2 or more patients. If the dose escalation portion of an arm is not stopped due to the occurrence of a DLT, it will be considered that the MTD has not been determined.

An optimal biological dose is also determined based on observed safety and tolerability, PK, PD, and preliminary antitumor activity.

The recommended dose for the expansion arms is determined based on review of the data used to determine the MTD and/or optimal biological dose.

The MTD, optimal biological dose, and recommended dose are independently determined for the single-agent arms and each combination therapy arm in the specific indication (NHL and ALL); up to 4 MTDs, optimal biological dose and recommended doses may be identified. The MTD for either combination therapy arm does not exceed the single-agent MTD DL, as the occurrence of DLTs in 2 patients for that single-agent DL, and the resulting determination of the MTD, preclude further dose escalation.

Study Duration

The study treatment period is from 6 to 12 months, depending on how an individual patient responds to treatment. The follow-up period is 6 months for all patients.

Sample size: Exact number of patients enrolled depend on the occurrence of protocol-defined DLTs and the number of DLs that will open. Sample size for single-agent REGN2810 dose escalation in lymphoma (B-NHL and HL) is up to 12 patients. Sample size for single-agent bsAb1 in patients with ALL is up to 42 patients (depending on which DL this arm opens at). Sample size for combination treatment dose escalation in patients with B-NHL is up to 42 patients (depending on which DL this arm opens at). Sample size for combination treatment dose escalation in patients with ALL is up to 42 patients (depending on which DL this arm opens at). Each expansion cohort will enroll 20 patients, for a total of 180 patients.

Study Treatments and Administration bsAb1 is supplied as a liquid in sterile, single-use vials. Each vial contains a withdrawable volume of 1 mL of bsAb1 at a concentration of 2 mg/mL. A pharmacist or other qualified individual is identified at each site to prepare bsAb1 for administration. The dose(s) received are according to dose level cohort assignment. The dose administered at each dose level is a flat dose and not dependent on patient weight or body surface area. Each dose of bsAb1 is administered by intravenous (IV) infusion over at least 60 minutes. The infusion time may be extended to up to 4 hours, per the physician's clinical judgment. Additionally, the investigator may choose to split the dose into 2 separate infusions over 2 (preferably consecutive) days.

REGN2810 is supplied as a liquid in sterile, single-use vials. Each vial contains a volume sufficient to withdraw 10 mL of REGN2810 at a concentration of 25 mg/mL. REGN2810 will be administered as a 30-minute IV infusion. Each patient's dose will depend on individual body weight. The dose of REGN2810 should be adjusted for changes in body weight of ≥10%. Dose adjustments for changes in body weight of <10% are at the discretion of the investigator.

On study visits in which both bsAb1 and REGN2810 are administered, REGN2810 is administered first.

Premedication with dexamethasone at least 1 hour prior to infusion is required prior to administration of bsAb1 at doses of 300 mcg or higher. At least 7.5 mg of dexamethasone is recommended with first administration of initial dose of bsAb1 and first administration of the subsequent higher dose (dose step). If the patient tolerates infusions without any signs or symptoms of infusion-related reaction or cytokine release syndrome (CRS), the investigator may lower or eliminate the dose of dexamethasone premedication administered prior to subsequent infusions, as needed based on clinical judgment. Premedication with anti-histamines and/or acetaminophen may also be considered. At doses lower than 300 mcg of bsAb1, empiric premedication with anti-histamines, acetaminophen and/or corticosteroids prior to study drug infusion is not recommended unless the patient has experienced infusion-related reactions or grade 2 or greater CRS with a previous infusion of bsAb1.

It is recommended that patients with ALL who are at high risk for cytokine release syndrome (CRS) and/or TLS (defined by ≥50% lymphoblasts in bone marrow; lactate dehydrogenase [LDH]≥500 U/L; or extramedullary involvement) receive a dexamethasone prophase. Dexamethasone prophase should be 10 mg/m2 every day (QD) for a minimum of 3 days and a maximum of 5 days. The dexamethasone prophase must be discontinued ≥72 hours prior to initiation of study drug(s).

At the time of relapse or progression, patients may be considered for retreatment. Patients with a sub-optimal response may also be considered for retreatment. The choice of retreatment (addition of REGN2810, bsAb1, or a higher dose of the treatment the patient is already receiving) will depend upon the initial treatment the patient received in the trial (e.g., single-agent bsAb1, REGN2810, or combination therapy), and which cohorts have cleared safety at the time the patient is considered for re-treatment. All decisions for retreatment will be made after discussion between the treating investigator and the sponsor. Retreatment will be at the highest DL that has been deemed safe and tolerable at the time of relapse or progression. Prior to retreatment, patients will be required to re-sign informed consent and meet eligibility criteria for re-treatment. For patients who received single-agent therapy, if the treating physician believes it is in the patient's best interest to receive combination therapy upon relapse or progression, the patient may cross-over to combination treatment at the combination dose level that has been deemed safe and tolerable at the time the patient is considered for re-treatment.

Study Endpoints

The primary endpoint is safety (specifically, adverse events [AEs], DLTs, safety laboratory data, and clinical findings). The secondary endpoints are: (i) PK of bsAb1 and REGN2810 when given alone and in combination; (ii) Immunogenicity: anti-bsAb1 and/or anti-REGN2810 antibodies; (iii) Antitumor activity: (a) Overall response rate as per applicable response criteria for the indication; (b) Duration of response, and progression-free survival at 6 and 12 months; (c) minimal residue disease (MRD) assessment for patients with bone marrow involvement at baseline; and (iv) Pharmacodynamic measures including cytokine profiling, peripheral blood B-cell and T-cell subsets and immune phenotyping, analysis of PD-1 occupancy of circulating T-cells, changes in gene expression in peripheral blood, and serum immunoglobulin.

Percentage change from baseline in the size of target tumor is also noted and summarized.

Procedures and Assessments

Screening procedures to be performed include cardiac ejection fraction, and brain MRI.

Safety procedures include medical history, physical examination, vital signs, electrocardiogram (ECG), coagulation, immune safety assays (for patients treated with REGN2810), assessment of B symptoms and evaluation of performance status, clinical laboratory tests, AEs, and concomitant medications.

Efficacy procedures to be performed for tumor assessments include CT or MRI scans, 18F-fluorodeoxyglucose-positron emission tomography (FDG-PET) scans, bone marrow aspirate and biopsies (BMA/Bx), lumbar puncture, lymph node and/or tumor biopsies.

Patients with NHL and with HL are assessed according to Cheson criteria (Cheson et al 2007, J. Clin. Oncol. 25(5): 579-86). Patients with fluorodeoxyglucose (FDG)-avid disease are also assessed according to the Lugano classification (Cheson et al 2014, J. Clin. Oncol 32:3059-3067). Patients with ALL are assessed according to the NCCN Guidelines 2014.

Assessment for presence of MRD in bone marrow samples is performed centrally by polymerase chain reaction (PCR). Determination of MRD response is performed per Brüggemann et al (Leukemia 2010, 24:521-35) in patients with ALL, follicular lymphoma, and marginal zone lymphoma.

Blood samples for PK and anti-drug antibody (ADA) assessment is collected.

Biomarkers samples are collected to monitor for changes in cytokine production, serum levels of pro-inflammatory cytokines, and changes in lymphocyte subsets and activation status. In addition, these samples permit tumor or somatic genetic analyses for variations that impact the clinical course of underlying disease or modulate treatment side effects.

Safety

An adverse event (AE) any untoward medical occurrence in a patient administered a study drug which may or may not have a causal relationship with the study drug. Therefore, an AE is any unfavorable and unintended sign (including abnormal laboratory finding), symptom, or disease which is temporally associated with the use of a study drug, whether or not considered related to the study drug. An AE also includes any worsening (i.e., any clinically significant change in frequency and/or intensity) of a preexisting condition that is temporally associated with the use of the study drug. Progression of underlying malignancy will not be considered an AE if it is clearly consistent with the typical progression pattern of the underlying cancer (including time course, affected organs, etc.). Clinical symptoms of progression may be reported as AEs if the symptom cannot be determined as exclusively due to the progression of the underlying malignancy, or does not fit the expected pattern of progression for the disease under study. A serious AE (SAE) is any untoward medical occurrence that at any dose results in death, is life-threatening, requires hospitalization, results in persistent or significant disability, and/or is an important medical event.

Patients are monitored for vital signs, general safety, cytokine release syndrome, B-cell depletion, CNS toxicity and for immune-mediated AEs.

Statistical Plan

Dose escalation cohorts: The study design is based on a traditional 3+3 design with 3 to 6 patients per DL.

Expansion cohorts: The sample size of 20 patients for each expansion cohort is determined based on the clinical consideration to further explore the safety of the RP2D in the expansion cohorts. The sample size of 20 patients also provides a preliminary evaluation on tumor response.

All AEs reported in this study are coded using the currently available version of the Medical Dictionary for Regulatory Activities (MedDRAR). Coding is to lowest level terms. The verbatim text, the preferred term (PT), and the primary system organ class (SOC) is listed.

Summaries of all treatment-emergent adverse events (TEAEs) by treatment arm include: (i) the number (n) and percentage (%) of patients with at least 1 TEAE by SOC and PT; (ii) TEAEs by severity, presented by SOC and PT; and (iii) TEAEs by relationship to treatment (related, not related), presented by SOC and PT. Deaths and other serious adverse events (SAEs) are listed and summarized by treatment arm. Treatment-emergent adverse events leading to permanent treatment discontinuation are listed and summarized by treatment arm.

Efficacy Analyses

Objective tumor response, determined by disease-relevant criteria, is summarized. The duration of response and progression-free survival at 6 and 12 months is listed and summarized by the Kaplan-Meier estimator, if needed. Minimal residue disease status is listed and summarized. Progression-free survival is listed and summarized. The percentage change from baseline in the size of the target tumor is also summarized.

Results

It is expected that the antibodies alone and in combination are safe and well-tolerated by patients. Administration of REGN2810 alone or in combination with bsAb1 is expected to inhibit tumor growth and/or promote tumor regression in patients with indolent or aggressive B-NHL or HL. It is expected that patients with ALL administered bsAb1 alone or in combination with REGN2810 will show tumor growth inhibition and/or remission. Overall response rate is expected to be better for combination therapy as compared to either monotherapy.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating or inhibiting the growth of a tumor comprising:
   (a) selecting a subject with B-cell cancer; and
   (b) administering to the subject in need thereof a therapeutically effective amount of an antibody or antigen-binding fragment thereof that specifically binds programmed death 1 (PD-1) in combination with a therapeutically effective amount of a bispecific antibody comprising a first antigen-binding arm that specifically binds CD20 and a second antigen-binding arm that specifically binds CD3; wherein:
   the anti-PD-1 antibody or antigen-binding fragment thereof is administered prior to or concurrent with the bispecific antibody;
   the anti-PD-1 antibody or antigen-binding fragment thereof comprises three heavy chain complementarity determining regions (CDRs) (HCDR1, HCDR2 and HCDR3) of a heavy chain variable region (HCVR) comprising the amino acid sequence of SEQ ID NO: 1 and three light chain CDRs (LCDR1, LCDR2 and LCDR3) of a light chain variable region (LCVR) comprising the amino acid sequence of SEQ ID NO: 2; and
   the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 11 and three light chain CDRs (LCDR1, LCDR2 and LCDR3) of a light chain variable region (LCVR) comprising the amino acid sequence of SEQ ID NO: 12; and the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 13 and three light chain CDRs (LCDR1, LCDR2 and LCDR3) of a light chain variable region (LCVR) comprising the amino acid sequence of SEQ ID NO: 12.

2. The method of claim 1, wherein the anti-PD-1 antibody comprises 0.1-20 mg/kg of the subject's body weight.

3. The method of claim 2, wherein the anti-PD-1 antibody comprises 0.3, 1, 3 or 10 mg/kg of the subject's body weight.

4. The method of claim 1, wherein the bispecific antibody comprises 0.1-10 mg/kg of the subject's body weight.

5. The method of claim 1, wherein the bispecific antibody comprises 10-8000 micrograms.

6. The method of claim 1, wherein the anti-PD-1 antibody is administered 1 week prior to the bispecific antibody.

7. The method of claim 1, wherein one or more doses of the anti-PD-1 antibody are administered in combination with one or more doses of the bispecific antibody.

8. The method of claim 7, wherein each dose of the anti-PD-1 antibody comprises 0.1-20 mg/kg of the subject's body weight.

9. The method of claim 8, wherein each dose of the anti-PD-1 antibody comprises 0.3, 1, 3, or 10 mg/kg of the subject's body weight.

10. The method of claim 7, wherein each dose of the bispecific antibody comprises 0.1-10 mg/kg of the subject's body weight.

11. The method of claim 8, wherein each dose of the bispecific antibody comprises 10-8000 micrograms.

12. The method of claim 11, wherein each dose of the anti-PD-1 antibody comprises 1, 3 or 10 mg/kg and each dose of the bispecific antibody comprises 30, 100, 300, 1000 or 2000 micrograms.

13. The method of claim 7, wherein each dose of the anti-PD-1 antibody is administered 0.5-12 weeks after the immediately preceding dose.

14. The method of claim 13, wherein each dose of the bispecific antibody is administered 0.5-12 weeks after the immediately preceding dose.

15. The method of claim 14, wherein each dose of the anti-PD-1 antibody is administered once in two weeks and each dose of the bispecific antibody is administered once a week.

16. The method of claim 7, wherein each dose of the bispecific antibody is split into 2-5 fractions within a dosing period.

17. The method of claim 1, wherein the anti-PD-1 antibody is administered 1 week prior to the bispecific antibody.

18. The method of claim 7, wherein the antibodies are administered intravenously, subcutaneously, or intraperitoneally.

19. The method of claim 1, wherein the B-cell cancer is selected from the group consisting of Hodgkin's lymphoma, non-Hodgkin's lymphoma, follicular lymphoma, small lymphocytic lymphoma, lymphoplasmacytoid lymphoma, marginal zone lymphoma, mantle cell lymphoma, diffuse large B-cell lymphoma, B-cell lymphomas, lymphomatoid granulomatosis, Burkitt's lymphoma, acute lymphoblastic leukemia, hairy cell leukemia, and B cell chronic lymphocytic leukemia.

20. The method of claim 1, wherein the subject is resistant or inadequately responsive to, or relapsed after prior therapy.

21. The method of claim 1, wherein the treatment produces a therapeutic effect selected from the group consisting of delay in tumor growth, reduction in tumor cell number, tumor regression, increase in survival, partial response, and complete response.

22. The method of claim 21, wherein tumor growth is delayed by at least 10 days as compared to an untreated subject.

23. The method of claim 1, wherein the tumor growth is inhibited by at least 50% as compared to an untreated subject.

24. The method of claim 7, wherein the tumor growth is inhibited by at least 50% as compared to a subject administered with either antibody as monotherapy.

25. The method of claim 7, wherein the tumor growth is inhibited by at least 50% as compared to a subject administered a bispecific anti-CD20/anti-CD3 antibody prior to an anti-PD-1 antibody.

26. The method of claim 7 further comprising administering to the subject a third therapeutic agent or therapy, wherein the third therapeutic agent or therapy is selected from the group consisting of radiation, surgery, a chemotherapeutic agent, a cancer vaccine, a PD-L1 inhibitor, a LAG-3 inhibitor, a CTLA-4 inhibitor, a TIM3 inhibitor, a BTLA inhibitor, a TIGIT inhibitor, a CD47 inhibitor, an indoleamine-2,3-dioxygenase (IDO) inhibitor, a vascular endothelial growth factor (VEGF) antagonist, an angiopoietin-2 (Ang2) inhibitor, a transforming growth factor beta (TGFβ) inhibitor, an epidermal growth factor receptor (EGFR) inhibitor, an antibody to a tumor-specific antigen, Bacillus Calmette-Guerin vaccine, granulocyte-macrophage colony-stimulating factor, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement.

27. The method of claim 1, wherein HCDR1 comprises the amino acid sequence of SEQ ID NO: 3; HCDR2 comprises the amino acid sequence of SEQ ID NO: 4; HCDR3 comprises the amino acid sequence of SEQ ID NO: 5; LCDR1 comprises the amino acid sequence of SEQ ID NO: 6; LCDR2 comprises the amino acid sequence of SEQ ID NO: 7; and LCDR3 comprises the amino acid sequence of SEQ ID NO: 8.

28. The method of claim 27, wherein the HCVR comprises the amino acid sequence of SEQ ID NO: 1 and the LCVR of the anti-PD-1 antibody comprises the amino acid sequence of SEQ ID NO: 2.

29. The method of claim 28, wherein the anti-PD-1 antibody comprises a heavy chain comprising the amino acid sequence of SEQ ID NO: 9 and a light chain comprising the amino acid sequence of SEQ ID NO: 10.

30. The method of claim 1, wherein A-HCDR1 comprises the amino acid sequence of SEQ ID NO: 14; A-HCDR2 comprises the amino acid sequence of SEQ ID NO: 15; A-HCDR3 comprises the amino acid sequence of SEQ ID NO: 16; LCDR1 comprises the amino acid sequence of SEQ ID NO: 17; LCDR2 comprises the amino acid sequence of SEQ ID NO: 18; and LCDR3 comprises the amino acid sequence of SEQ ID NO: 19.

31. The method of claim 30, wherein the A-HCVR comprises the amino acid sequence of SEQ ID NO: 11 and the LCVR comprises the amino acid sequence of SEQ ID NO: 12.

32. The method of claim 1, wherein B-HCDR1 comprises the amino acid sequence of SEQ ID NO: 20; B-HCDR2 comprises the amino acid sequence of SEQ ID NO: 21; B-HCDR3 comprises the amino acid sequence of SEQ ID NO: 22; LCDR1 comprises the amino acid sequence of SEQ ID NO: 17; LCDR2 comprises the amino acid sequence of SEQ ID NO: 18; and LCDR3 comprises the amino acid sequence of SEQ ID NO: 19.

33. The method of claim 32, wherein the B-HCVR comprises the amino acid sequence of SEQ ID NO: 13 and the LCVR of the bispecific antibody comprises the amino acid sequence of SEQ ID NO: 12.

* * * * *